(12) United States Patent
Barber, III et al.

(10) Patent No.: US 10,433,493 B2
(45) Date of Patent: Oct. 8, 2019

(54) CONTROLLING ULTRAVIOLET INTENSITY OVER A SURFACE OF A LIGHT SENSITIVE OBJECT

(71) Applicant: Sensor Electronic Technology, Inc., Columbia, SC (US)

(72) Inventors: Arthur Peter Barber, III, Columbia, SC (US); Maxim S. Shatalov, Columbia, SC (US); Alexander Dobrinsky, Silver Spring, MD (US); Michael Shur, Latham, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 15/711,291

(22) Filed: Sep. 21, 2017

(65) Prior Publication Data

US 2018/0092308 A1    Apr. 5, 2018

Related U.S. Application Data

(60) Provisional application No. 62/403,003, filed on Sep. 30, 2016.

(51) Int. Cl.
*A01G 7/04* (2006.01)
*G01J 1/16* (2006.01)
(Continued)

(52) U.S. Cl.
CPC .............. *A01G 7/045* (2013.01); *A01G 9/20* (2013.01); *A23B 7/015* (2013.01); *A23L 3/28* (2013.01);
(Continued)

(58) Field of Classification Search
CPC .......... A01G 7/045; A01G 9/20; A23B 7/015; G01J 1/0228; G01J 1/10; G01J 1/16;
(Continued)

(56) References Cited

U.S. PATENT DOCUMENTS 7,553,456 B2 * 6/2009 Gaska ...................... A61L 2/10
422/121
7,634,996 B2   12/2009 Gaska et al.
(Continued)

OTHER PUBLICATIONS

Muller-Xing, R., "Footprints of the sun: memory of UV and light stress in plants," Frontiers in Plant Science, vol. 5 (Sep. 2014), pp. 1-11.

*Primary Examiner* — Michael C Bryant
(74) *Attorney, Agent, or Firm* — LaBatt, LLC

(57) ABSTRACT

An approach for controlling ultraviolet intensity over a surface of a light sensitive object is described. Aspects involve using ultraviolet radiation with a wavelength range that includes ultraviolet-A and ultraviolet-B radiation to irradiate the surface. Light sensors measure light intensity at the surface, wherein each sensor measures light intensity in a wavelength range that corresponds to a wavelength range emitted from at least one of the sources. A controller controls the light intensity over the surface by adjusting the power of the sources as a function of the light intensity measurements. The controller uses the light intensity measurements to determine whether each source is illuminating the surface with an intensity that is within an acceptable variation with a predetermined intensity value targeted for the surface. The controller adjusts the power of the sources as a function of the variation to ensure an optimal distribution of light intensity over the surface.

20 Claims, 9 Drawing Sheets

(51) Int. Cl.
  *G01J 1/24* (2006.01)
  *G01J 1/20* (2006.01)
  *G01J 1/02* (2006.01)
  *G01J 1/10* (2006.01)
  *G01J 1/42* (2006.01)
  *G01J 1/26* (2006.01)
  *A01G 9/20* (2006.01)
  *A23B 7/015* (2006.01)
  *A23L 3/28* (2006.01)
  *G01N 21/64* (2006.01)
  *H05B 37/02* (2006.01)
  *H05B 33/08* (2006.01)

(52) U.S. Cl.
  CPC .............. *G01J 1/0228* (2013.01); *G01J 1/10* (2013.01); *G01J 1/16* (2013.01); *G01J 1/20* (2013.01); *G01J 1/24* (2013.01); *G01J 1/26* (2013.01); *G01J 1/42* (2013.01); *G01J 1/429* (2013.01); *G01N 21/6486* (2013.01); *H05B 33/0854* (2013.01); *H05B 37/0227* (2013.01); *H05B 37/0281* (2013.01); *G01J 2001/1657* (2013.01); *G01J 2001/4252* (2013.01); *Y02P 60/149* (2015.11)

(58) Field of Classification Search
  CPC ........ G01J 1/20; G01J 1/24; G01J 1/26; G01J 1/42; G01J 1/429; G01N 21/6486
  See application file for complete search history.

(56) References Cited

U.S. PATENT DOCUMENTS

| | | | |
|---|---|---|---|
| 8,277,734 B2 | 10/2012 | Koudymov et al. | |
| 8,980,178 B2 | 3/2015 | Gaska et al. | |
| 9,006,680 B2 | 4/2015 | Bettles et al. | |
| 9,034,271 B2 | 5/2015 | Shur et al. | |
| 9,061,082 B2 | 6/2015 | Gaska et al. | |
| 9,138,499 B2 | 9/2015 | Bettles et al. | |
| 9,179,703 B2 | 11/2015 | Shur et al. | |
| 9,550,004 B2 | 1/2017 | Smetona et al. | |
| 9,572,903 B2 | 2/2017 | Dobrinsky et al. | |
| 9,603,960 B2 | 3/2017 | Dobrinsky et al. | |
| 9,687,577 B2 | 6/2017 | Dobrinsky et al. | |
| 9,707,307 B2 | 7/2017 | Shur et al. | |
| 9,718,706 B2 | 8/2017 | Smetona et al. | |
| 9,724,441 B2 | 8/2017 | Shur et al. | |
| 9,750,830 B2 | 9/2017 | Shur et al. | |
| 9,757,486 B2 | 9/2017 | Dobrinsky et al. | |
| 9,795,699 B2 | 10/2017 | Shur et al. | |
| 9,801,965 B2 | 10/2017 | Bettles et al. | |
| 9,802,840 B2 | 10/2017 | Shturm et al. | |
| 9,878,061 B2 | 1/2018 | Shur et al. | |
| 9,919,068 B2 | 3/2018 | Shur et al. | |
| 9,974,877 B2 | 5/2018 | Bettles et al. | |
| 9,981,051 B2 | 5/2018 | Shur et al. | |
| 9,987,383 B2 | 6/2018 | Bilenko et al. | |
| 9,999,782 B2 | 6/2018 | Shur et al. | |
| 10,004,821 B2 | 6/2018 | Dobrinsky et al. | |
| 10,040,699 B2 | 8/2018 | Smetona et al. | |
| 10,099,944 B2 | 10/2018 | Smetona et al. | |
| 2010/0115830 A1* | 5/2010 | Dube | A01G 7/045 47/17 |
| 2012/0126134 A1* | 5/2012 | Deal | A61L 2/10 250/372 |
| 2013/0048545 A1 | 2/2013 | Shatalov et al. | |
| 2014/0202962 A1 | 7/2014 | Bilenko et al. | |
| 2016/0074548 A1 | 3/2016 | Dobrinsky et al. | |
| 2016/0114186 A1 | 4/2016 | Dobrinskly et al. | |
| 2016/0345512 A1* | 12/2016 | Wargent | H05B 33/0869 |
| 2017/0057842 A1 | 3/2017 | Dobrinskly et al. | |
| 2017/0100495 A1 | 4/2017 | Shur et al. | |
| 2017/0189711 A1 | 7/2017 | Shur et al. | |
| 2017/0192154 A1* | 7/2017 | Gilley | A01G 7/045 |
| 2017/0245527 A1 | 8/2017 | Dobrinsky et al. | |
| 2017/0245616 A1 | 8/2017 | Lakios et al. | |
| 2017/0281812 A1 | 10/2017 | Dobrinsky et al. | |
| 2017/0290934 A1 | 10/2017 | Dobrinsky et al. | |
| 2017/0368215 A1 | 12/2017 | Shatalov et al. | |
| 2018/0028700 A1 | 2/2018 | Dobrinsky et al. | |
| 2018/0054975 A1 | 3/2018 | Shur et al. | |
| 2018/0180550 A1* | 6/2018 | Franjic | G01B 9/02091 |

* cited by examiner

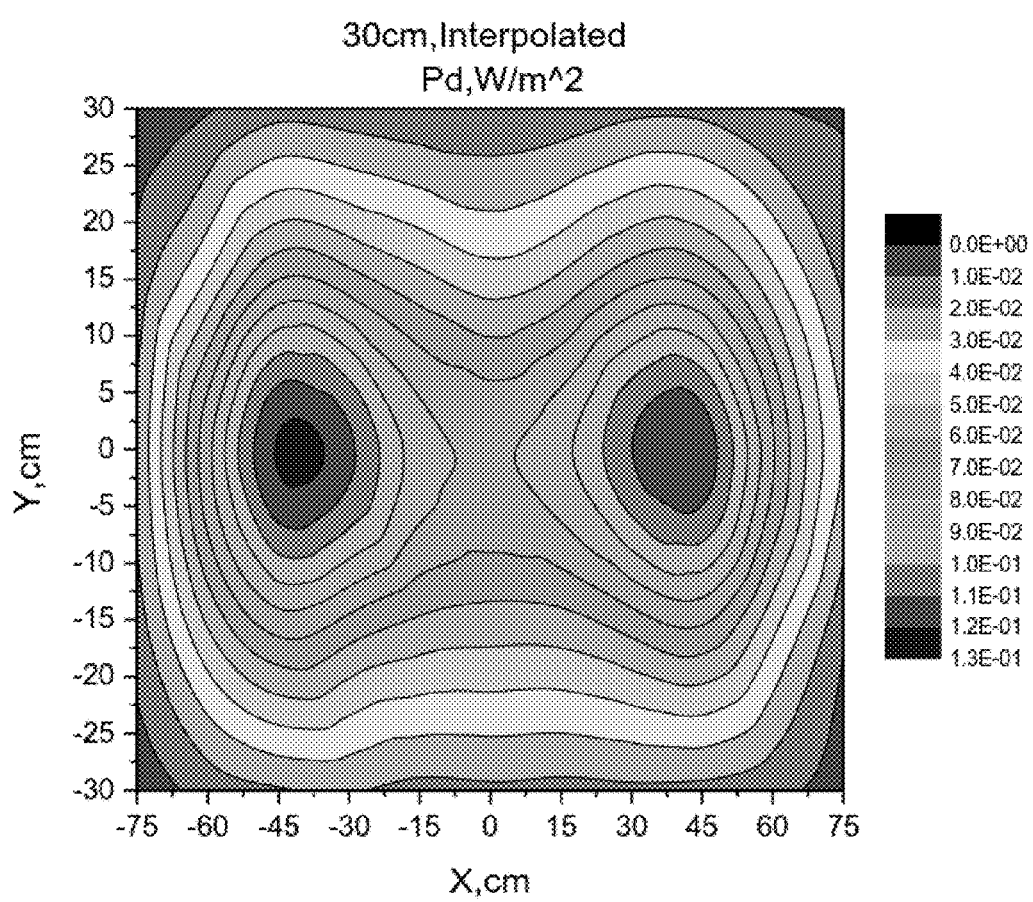

CONTROLLING ULTRAVIOLET INTENSITY OVER A SURFACE OF A LIGHT SENSITIVE OBJECT

REFERENCE TO RELATED APPLICATIONS

The present patent application claims the benefit of U.S. Provisional Application No. 62/403,003, filed on 30 Sep. 2016, and which is hereby incorporated by reference. The application is also related U.S. application Ser. No. 15/678,456, filed on 16 Aug. 2017.

TECHNICAL FIELD

The present invention relates generally to controlled lighting environments, and more particularly, to a smart lighting system that utilizes light sensors to detect light intensity at a surface of a light sensitive object, and a controller that receives feedback from the light sensors and controls the light intensity over the surface to within an acceptable variation in order to attain an acceptable light intensity distribution.

BACKGROUND ART

A plant is one type of light sensitive object that can be grown in a controlled light environment. Growing plants under controlled conditions such as in greenhouses, growth cabinets or warehouses, generally entails monitoring the plant environment and controlling parameters such as light, water vapor pressure, temperature, $CO_2$ partial pressure, and air movement, in order to adjust the microclimate of the environment for optimizing growth and photosynthesis in an empirical manner. Plant attributes such as quantitative morphological, physiological and biochemical characteristics of at least a part of the plant may also be modulated during the monitoring of the plant environment and controlling of environment parameters.

Having the ability to determine the physiological condition of a plant or a group of plants is useful in implementing photosynthetic responses into climate control algorithms or models that can be used in a controlled light environment. Optimization of photosynthesis of crops or plant material can be achieved through careful and planned manipulations of growth conditions based on in-situ monitoring of relevant photosynthetic processes. Relevant and short-term plant responses are involved in the definition of growth requirements not only through climate control, but also through the production processes, fertilizers, light quality, light intensity, and crop quality.

To effectively control the climate, irrigation, nutrition and light regime of greenhouse crops in order to beneficially modulate and control growth and attributes of crops, sensors as well as models can be incorporated into a feed-forward/feedback component of a lighting system. Feed-forward controllers can use lamp light output to provide the necessary input for plant growth and have the capacity to anticipate the effects of disturbances on the greenhouse climate and in the light environment and take action within precisely set limits. Specific crop models, developed for individual crop species, can be based on data from sensors and used to estimate the benefits of changing growth regimes (e.g., spectral quality of the light source) to influence or modulate the outcome (e.g., flowering time). To this extent, the data obtained by the sensors can be combined with model-based algorithms in a lighting system to direct specific changes that influence the plant's growth processes or attributes.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to a lighting system that incorporates optimal irradiation settings to irradiate a surface of the light sensitive object under a variety of environmental conditions with various radiation sources, light sensors to detect light intensity at the surface, and a controller that controls the power of the radiation sources irradiating the surface of the object according to feedback from the sensors. In this manner, the irradiation of the surface can be optimized to attain desired characteristics such as a predetermined light intensity distribution pattern that is formed over the surface of the object.

Various radiation sources can be used to irradiate the light sensitive object. In one embodiment, an array of ultraviolet radiation sources can be used to irradiate a surface of the object with ultraviolet radiation having a wavelength range that includes ultraviolet-A (UV-A) radiation and ultraviolet-B (UV-B) radiation. In another embodiment, a set of visible light sources can irradiate the surface of the object with visible radiation in conjunction with the ultraviolet radiation sources. In still another embodiment, an infrared source can irradiate the surface of the object with infrared radiation in addition to the ultraviolet radiation sources and the visible radiation sources.

Many different configurations of radiation sources are possible for an embodiment that uses an array of ultraviolet radiation sources with a set of visible light sources and an infrared source. For example, the array of ultraviolet radiation sources can include a UV-A source operating at a peak wavelength of 365 nm with a full width half max ranging from 5 nm to 10 nm, and a UV-B source operating in a wavelength range of 280 nm to 300 nm. The set of visible light sources and infrared source can include a dark blue light source operating in a wavelength range of 440 nm to 450 nm; a blue light source operating at a peak wavelength of 470 nm with a full width half max ranging from 5 nm to 10 nm; a green light source operating in a wavelength range of 525 nm to 540 nm; a red light source operating in a wavelength range of 620 nm to 640 nm; and an infrared source operating in a wavelength range of 725 nm to 740 nm.

A set of light sensors can measure the light intensity at the surface of the object. In one embodiment, each light sensor can measure light intensity in a wavelength range that corresponds to a predetermined wavelength range emitted from one of the sources that irradiates the object. The light sensors can include, but are not limited to, photodetectors, photodiodes, and visible light cameras.

A controller can control the power of the radiation sources irradiating the surface of the object according to feedback data received from the light sensors. In this manner, the controller can control the light intensity over the surface of the object as a function of light intensity measurements obtained from the light sensors. In one embodiment, the controller can use the light intensity measurements to determine whether each source is illuminating the surface of the object at a dose that delivers the radiation at an intensity that is within an acceptable variation of a predetermined intensity value targeted for the surface. The controller can adjust the power of each source in response to determining that the source is illuminating the surface with an intensity that has an unacceptable variation with the predetermined intensity value targeted for the surface. In this manner, the controller can adjust the power of the sources to attain a predetermined light intensity distribution over the surface. The predetermined intensity distribution can include a variety of different patterns. For example, the predetermined intensity distribution can include individual peaks of intensity with each corresponding to one of the sources irradiating the surface. In one embodiment, the predetermined intensity distribution can include a set of points along the surface that have a minimal difference in intensity between the points. In another embodiment, the predetermined intensity distribution can include regions located along the surface with varying patterns, types of radiation, wavelengths, dosages, and/or intensities. For example, outer regions of the surface can have higher light intensities than the intensities at a central region of the surface.

In one embodiment, fluorescent sources can be used to irradiate the surface of the object in conjunction with any other radiation sources that are used to irradiate the object. Fluorescent sensors can be used to detect fluorescent radiation reflected from the surface of the object. In one embodiment, the fluorescent sources and the fluorescent sensors can operate in a pulsed regime to differentiate from fluorescent signals reflected from the surface that arise from the irradiation by the other radiation sources.

Light reflectance sensors also can be used to detect radiation reflected from the surface of the object, including fluorescent and/or infrared radiation. In one embodiment, the light reflectance sensors can detect reflected radiation that has time dependent characteristics such as radiation that is generated from sources operating in a pulsed regime. In this manner, the light reflectance sensors can measure a phase-shift and/or a wavelength-shift of the reflected radiation from the surface.

A first aspect of the invention provides a lighting system, comprising: an array of ultraviolet radiation sources configured to irradiate a surface of a light sensitive surface object with ultraviolet radiation having a wavelength range that includes ultraviolet-A (UV-A) radiation and ultraviolet-B (UV-B) radiation, wherein each of the ultraviolet radiation sources operates in a predetermined wavelength range that includes at least one of: a UV-A radiation wavelength range or a UV-B radiation wavelength range, wherein at least one of the ultraviolet radiation sources operates at a peak wavelength that is within the UV-B wavelength range; a plurality of light sensors configured to measure light intensity at the surface of the object, wherein each light sensor measures light intensity in a wavelength range that corresponds to the predetermined wavelength range emitted from at least one of the ultraviolet radiation sources in the array; and a controller configured to control the light intensity over the surface of the object by adjusting operational power of the ultraviolet radiation sources as a function of light intensity measurements obtained by the light sensors, wherein the controller uses the light intensity measurements to determine whether each ultraviolet radiation source is illuminating the surface of the object with an intensity that has a variation that is more than 50% of a predetermined intensity value targeted for the surface, the controller adjusting the power of an ultraviolet radiation source in response to determining that the ultraviolet radiation source is illuminating the surface of the object with an intensity that has a variation that is more than 50% of the predetermined intensity value targeted for the surface, the controller adjusting the power of the ultraviolet radiation source as a function of the variation between the light intensity generated from the source and the predetermined intensity value targeted for the surface.

A second aspect of the invention provides a lighting system, comprising: an array of ultraviolet radiation sources configured to irradiate a surface of a light sensitive object with ultraviolet radiation having a wavelength range that includes ultraviolet-A (UV-A) radiation and ultraviolet-B (UV-B) radiation, wherein each of the ultraviolet radiation sources irradiates the surface of the object with ultraviolet radiation over a predetermined wavelength range, and at least one of the ultraviolet radiation sources operates at a peak wavelength that is within a UV-B wavelength range; a plurality of light sensors configured to measure light intensity at the surface of the object, wherein each light sensor measures light intensity in a wavelength range that corresponds to the predetermined wavelength range emitted from at least one of the ultraviolet radiation sources in the array; and a controller configured to control the light intensity over the surface of the object as a function of light intensity measurements obtained from the light sensors, wherein the controller uses the light intensity measurements to determine whether each ultraviolet radiation source is illuminating the surface of the object at a dose that delivers the ultraviolet radiation at an intensity that is within a predetermined acceptable variation with a maximum intensity value targeted for the surface, the controller adjusting the power of each ultraviolet radiation source in response to determining that the ultraviolet radiation source is illuminating the surface with an intensity that has an unacceptable variation with the maximum intensity value targeted for the surface, each ultraviolet radiation source that is adjusted in power delivers an adjusted dose of the ultraviolet radiation that is a function of an amount of the variation with the maximum intensity value that is unacceptable.

A third aspect of the invention provides a system for irradiating a plant, comprising: a set of visible light sources configured to irradiate the plant with visible radiation having a range of visible wavelengths; a set of infrared radiation sources configured to irradiate the plant with infrared radiation having a range of infrared wavelengths; a set of ultraviolet radiation sources configured to irradiate the plant with ultraviolet radiation having a range of ultraviolet wavelengths; a plurality of light sensors configured to measure light intensity at a surface of the plant, wherein each light sensor measures light intensity in a wavelength range that corresponds to the range of wavelengths emitted from at least one of the sets of visible light sources, infrared sources, or ultraviolet radiation sources; and a controller configured to control the irradiation of the plant by the sets of visible light sources, infrared radiation sources, and ultraviolet radiation sources, the controller directing the sets of visible light sources, infrared radiation sources and ultraviolet radiation sources to provide a predetermined distribution of light intensity over the plant, the controller adjusting the power of the radiation sources and a direction that the radiation from the radiation sources irradiates the plant as a function of light intensity measurements obtained from the light sensors to maintain the predetermined uniform distribution of light intensity over the plant.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 5A-5B show measured light intensity distributions obtained from a lighting system described herein according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
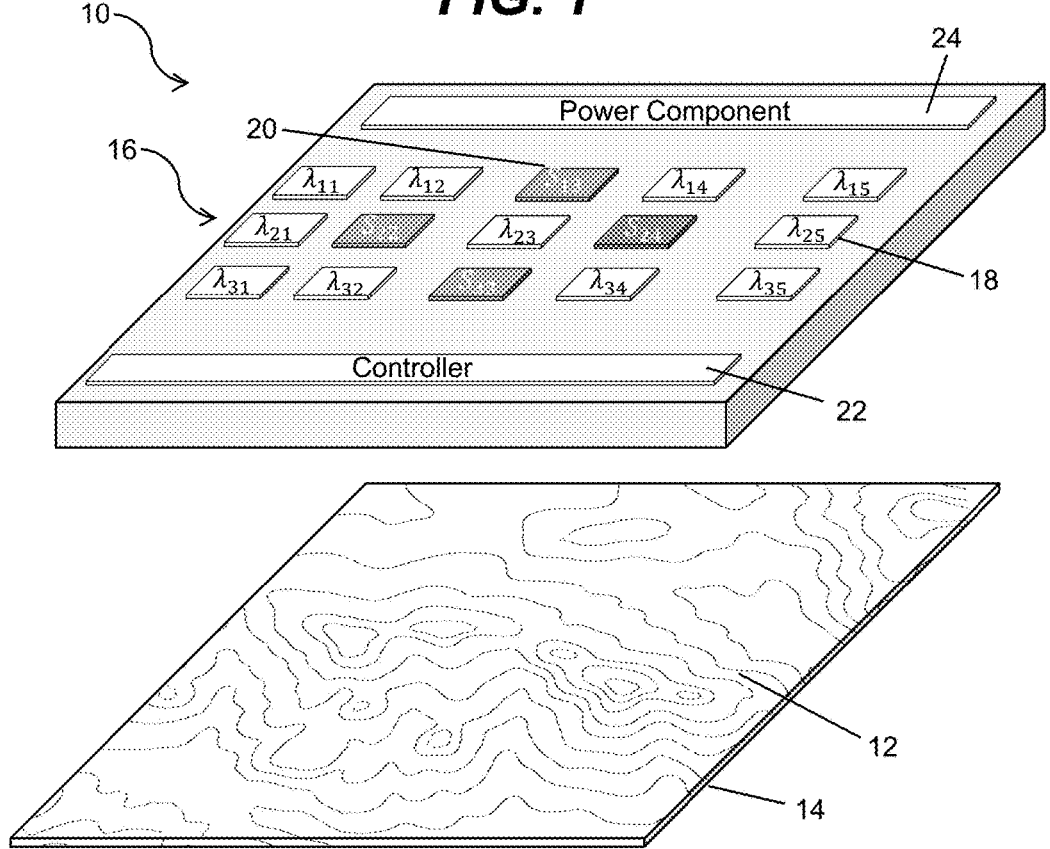
FIG. 1 shows a schematic of a lighting system for irradiating a surface of a light sensitive object at a predetermined light intensity distribution according to an embodiment.

As indicated above, aspects of the present invention are directed to a lighting system that incorporates optimal irradiation settings to irradiate a surface of the light sensitive object under a variety of environmental conditions with various radiation sources, light sensors to detect light intensity at the surface, and a controller that controls the power of the radiation sources irradiating the surface of the object according to feedback from the sensors in order to attain desired characteristics such as a predetermined light intensity distribution pattern over the surface of the object.

In one embodiment, the light sensitive object can include a living organism such as a plant. As used herein, a plant can include any one of a vast number of organisms within the biological kingdom Plantae. In general, a plant includes species that are considered of limited motility and generally manufacture their own food. A non-exhaustive list of plants can include, but are not limited to, vegetables, flowers, trees, forbs, shrubs, grasses, vines, ferns, and mosses. In one embodiment, various radiation sources can be used to irradiate parts of the plant such as leaves, a canopy of leaves, branches, trunks, roots, nodes and buds. Although the description that follows is mainly directed to a plant, various embodiments of the present invention are suitable for use with any light sensitive object where it is desirable to irradiate a surface of the object to alter chemical and biological processes internal to the object in order to impart certain physiological responses. Examples of other light sensitive objects that are suitable for use with a lighting system that incorporates the concepts of the various embodiments described herein can include, but is not limited to, living organisms such as plants, humans and animals, as well as surfaces having a composition (e.g., coating) that can undergo chemical/structural change due to radiation.

The various embodiments for controlling the light intensity of radiation irradiating a light sensitive object with a lighting system described herein can include a number of components, some of which may not be included in embodiments. These components and the functions that each can perform are described below in more detail. The components and actions can include any now known or later developed approaches that can facilitate implementation of the concepts and configurations of the various embodiments described herein.

As used herein, controlling the light intensity of radiation while irradiating a light sensitive object means modifying the intensity of light at different locations of the irradiated surface(s) of the light sensitive object. Generally, controlling light exposure of a light sensitive object entails controlling the intensity of radiation, duration of radiation, the wavelength(s) of radiation, and/or the time schedule of radiation intensity and wavelength.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The description that follows may use other terminology herein for the purpose of describing particular embodiments only, and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It will be further understood that the terms "comprises," "comprising," "includes," "including," "has," "have," and "having" when used in this specification, specify the presence of stated features, integers, steps, operations, elements, and/or components, but do not preclude the presence or addition of one or more other features, integers, steps, operations, elements, components, and/or groups thereof.

In the current description, "uniform" refers to variance of less than ten percent. For example, a distribution of intensity over a surface and intensity over a surface are uniform when the intensity varies over the surface by less than ten percent. In general, the actual intensity may deviate from uniform intensity over a surface. The variance (deviation) can be measured as a ratio between a difference in the highest and lowest intensity values and the highest intensity value measured in percent as observed over the surface of the irradiated object. As used herein, a setting, value, configuration, and/or the like, is considered "optimal" when it is configured to provide the best result for the corresponding purpose(s) considering all the parameters and using the given system. To this extent, optimal does not mean or imply that the result is the best achievable in a hypothetical, idealized system or the best achievable using different considerations and/or parameters. As used herein, unless otherwise noted, the term "approximately" is inclusive of values within +/−ten percent of the stated value.

Turning to the drawings, FIG. 1 shows a schematic of a lighting system 10 for irradiating a surface 12 of a light sensitive object 14 with a predetermined light intensity distribution according to an embodiment. The light sensitive object 14 can include, for example, a surface of a plant, fruit, or vegetable, a film surface sensitive to irradiation, and/or the like. It is understood, that other objects that have surfaces that are sensitive to light are suitable for use in this embodiment. For example, objects such as human skin, surfaces containing bacteria or microorganisms, and/or the like, are suitable for irradiation with the lighting system 10.

In one embodiment, the lighting system 10 can include an array 16 of ultraviolet radiation sources 18 configured to irradiate the surface 12 of the object 14 with ultraviolet radiation having a wavelength range that can include UV-A radiation and UV-B radiation. For example, each ultraviolet radiation source 18 can operate in a predetermined wavelength range that includes at least one of: a UV-A radiation wavelength range or a UV-B radiation wavelength range. In one embodiment, at least one of the ultraviolet radiation sources 18 can operate at a peak wavelength that is within the UV-B wavelength range.

The ultraviolet radiation sources 18 can be arranged to irradiate the surface 12 of the object 14 in a variety of approaches. For example, each of the ultraviolet radiation sources can irradiate a different region (e.g., spot) along the surface 12 of the object 14. In one embodiment, the ultraviolet radiation sources 18 can irradiate each region with relatively uniform radiation. In another embodiment, more than one ultraviolet radiation source 18 can be used to irradiate a single region on the object, with each irradiating the common region at a different intensity of radiation. In order to facilitate spot irradiation performed by the ultraviolet radiation sources 18, a set of reflective optical elements can be used to focus the ultraviolet radiation to regions on the surface 12 of the object 14. In one embodiment, each optical element can be configured to focus ultraviolet radiation emitted from one of the ultraviolet radiation sources to a respective region on the object 12. Examples of optical elements that can be used in conjunction with the ultraviolet radiation sources 18 can include, but are not limited to, a lens and/or a set of lenses.

In one embodiment, the array 16 of ultraviolet radiation sources 18 can be configured for movement about the object 14 to attain one of a number of targeted intensity distributions over the surface 12 of the object 14. For example, each of the ultraviolet radiation sources 18 can be implemented to have movement in both translational and directional degrees of freedom. In one embodiment, the ultraviolet radiation sources 18 can be implemented to have movement in both translational and directional degrees of freedom by, for example, sliding on a railing system. In an embodiment, the array 16 of ultraviolet radiation sources 18 can have rotational degree of freedom and rotate around its center around a chosen axis.

In one embodiment, the array 16 of ultraviolet radiation sources 18 can be configured to have a greater amount of ultraviolet radiation sources (e.g., a higher density of ultraviolet radiation sources) located at side portions of the array in comparison to an amount of ultraviolet radiation sources located near a central region of the array. For example, the side portions of the array 16 can include at least 10% more ultraviolet radiation sources (e.g., a density of ultraviolet radiation sources at least 10% higher) than the amount of ultraviolet radiation sources 18 located near the central region. In one embodiment, the ultraviolet radiation sources 18 located at the side portions of the array 16 can operate at a higher pulsed frequency than the ultraviolet radiation sources located near the central region. In one embodiment, the ultraviolet radiation sources 18 located at the side portions of the array 16 can operate at a higher power than the ultraviolet radiation sources located near the central region.

The lighting system 10 can further include a set of light sensors 20, each of which is configured to measure light intensity at the surface 12 of the object 14. In one embodiment, each light sensor 20 can measure light intensity in a wavelength range that corresponds to the predetermined wavelength range emitted from at least one of the ultraviolet radiation sources 18 in the array 16. As shown in FIG. 1, the light sensors 20 can be located within and/or interchanged with the array 16 of ultraviolet radiation sources 18. For example, in one embodiment, the array 16 can include a 3×5 array with ultraviolet radiation sources 18 in locations 1,1; 1,2; 1,4; 1,5; 2,1; 2,3; 2,5; 3,1; 3,2; 3,4; and 3,5 of the array; while the light sensors 20 can occupy locations 1,3; 2,2; 2,4 and 3,3. It is understood, the locations of the ultraviolet radiation sources 18 and the light sensors 20 in the array 16, as well as the amount of each are only illustrative of one possible implementation and are not meant to be limiting. Further, it is understood that the light sensors 20 can be configured in the lighting system 10 apart from the array 16 of ultraviolet radiation sources 18. For example, the light sensors 20 can be located above, below, and/or to the side of the array 16.

The lighting system 10 can further include a controller 22 that is configured to control the light intensity over the surface 12 of the object 14. In particular, the controller 22 can control the light intensity over the surface 12 by adjusting the operational power of the ultraviolet radiation sources 18 as a function of the light intensity measurements obtained by the light sensors 20. In one embodiment, the controller 22 can use the light intensity measurements to determine whether each ultraviolet radiation source 18 is illuminating the surface 12 of the object 14 with an intensity that has a relatively small deviation from uniformity. In general, a deviation from uniformity that is more than 50% is indicative of poor intensity uniformity. In such cases, the controller 22 can adjust the intensity of one or more of the individual ultraviolet radiation sources 18 to increase the uniformity of the light intensity.

The controller 22 can adjust the power of each ultraviolet radiation source 18, via a power component 24 that powers the lighting system 10, in response to determining that the ultraviolet radiation source is illuminating the surface 12 of the object 14 in a manner that does not satisfy a predetermined objective. In one embodiment, the controller 22 can adjust the power of each ultraviolet radiation source 18 in response to determining that the ultraviolet radiation source is illuminating the surface of the object with an intensity that has a variation that is more than 50% of the predetermined intensity value targeted for the surface. In another embodiment, the controller 22 can adjust the power of each ultraviolet radiation source 18 in response to determining that the ultraviolet radiation source is illuminating the surface of the object with an overall dose that has a variation that is more than 50% of the predetermined intensity value targeted for the surface. The controller 22 can assess whether any of these predetermined objectives are being met for each particular wavelength that is used to irradiate the surface 12 of the object 14. It is understood that each predetermined objective can be different for each wavelength of light used for irradiation of the surface 12. In general, the operation of the lighting system 10 and the fulfillment of the objectives will depend on the distance to the surface 12 of the object 14 from the system, the overall operational environment of the system including the presence of other surfaces capable of altering the overall radiation pattern of the surface, and the light properties of the surface.

In one embodiment, the controller 22 can adjust the power of each ultraviolet radiation source 18 that is powered by the power component 24 as a function of the variation between the light intensity generated from the source and the predetermined intensity value targeted for the surface. In particular, the resultant intensity from the array of radiation sources 16 is compared to the target intensity and the intensity of one or more sources 18 can be adjusted according to a radiation model to achieve the target intensity. The radiation model can comprise a computer ray tracing simulation model, which can be implemented as a data table that lists intensity distribution for a given set of intensities of sources 18.

In one embodiment, the controller 22 can adjust the ultraviolet radiation sources 18 to achieve other targeted objectives associated with the intensity of radiation provided to the surface 12 of the object 14. For example, the controller 22 can control the ultraviolet radiation sources 18, via the power component 24, to provide higher intensity delivered to the outer edges of the surface 12 of the object 14, and lower intensity radiation as compared to the intensity delivered to the outer edges irradiating the central inner portions of the surface. Controlling some of the ultraviolet radiation sources 18 to operate with more power and others to operate at less power in order to have high intensity radiation at the outer edges of the surface with low intensity radiation at the central portion can result in better uniformity over an area of the object 14.

In one embodiment, the controller 22 can adjust the ultraviolet radiation sources 18 based on the feedback measurements provided by the sensors to achieve a targeted dose objective for each of the ultraviolet radiation sources 18 irradiating the surface 12 of the object 14. For example, the controller 22 can control the ultraviolet radiation sources 18 to operate at different pulsed frequencies. In this case, the ultraviolet radiation sources 18 can be operated to repeatedly emit ultraviolet radiation for a duration of time followed by a duration of time during which no radiation is emitted. In one embodiment, the controller 22 can instruct some of the ultraviolet radiation sources 18 to operate at a higher pulsed frequency and others to operate at a lower pulsed frequency as compared to the higher pulsed frequency. In one example, the controller 22 can control the ultraviolet radiation sources 18 configured to irradiate the outer edge of the surface 12 of the object 14 to operate a higher frequency, and have those sources configured to irradiate the central portion of the surface operate a lower frequency. Operating the ultraviolet radiation sources 18 in this manner can be beneficial because different pulsed frequencies at different locations results in delivering different radiation doses at different locations. This can be beneficial depending on the application of the ultraviolet radiation. For instance, in the case of ultraviolet ink curing, the edges of the ink region might require a higher dose of radiation for faster ink curing whereas smaller doses of radiation can be used within the domain.

In one embodiment, the controller 22 can use the data from the sensors 20 to control the light intensity over the surface 12 of the object 14 that is provided by the ultraviolet radiation sources 18 to maintain a predetermined intensity distribution. In one example, the predetermined intensity distribution can include a set of points located along the surface 12 that have a minimal difference in intensity. As used herein, a minimal difference in intensity means that the intensity is uniform. In particular, the controller 22 can receive light intensity measurements from the light sensors 20 that are configured to obtain light intensity data for that area of the surface 12 that encompasses the set of points. If the intensity measurements from these light sensors 20 are not within an acceptable variation, then the controller can adjust the power output of any of the sources irradiating that region to ensure that each is providing an intensity that is acceptable. The controller 22 will continue to monitor the intensity measurements from these sets of points and make adjustments to the sources 18 as needed. The controller 22 can continue with this monitoring and adjusting until it is time to stop the operation. Having a set of points located along the surface that receive essentially the same intensity ensures that the region of the surface 12 of the object 14 that contains the point will have uniform intensity.

In one embodiment, the ultraviolet radiation sources 18 can comprise any combination of one or more types of ultraviolet radiation emitters. Examples of an ultraviolet radiation emitter can include, but are not limited to, high intensity ultraviolet lamps (e.g., high intensity mercury lamps), discharge lamps, ultraviolet LEDs, super luminescent LEDs, laser diodes, light emitting sources, solid state light sources, and/or the like. In one embodiment, the ultraviolet radiation sources can include a set of LEDs manufactured with one or more layers of materials selected from the group-III nitride material system (e.g., $Al_xIn_yGa_{1-x-y}N$, where $0 \leq x, y \leq 1$, and $x+y \leq 1$ and/or alloys thereof). Additionally, the ultraviolet radiation sources 18 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures can include, but are not limited to, a wave guide, a plurality of ultraviolet fibers, each of which terminates at an opening, a diffuser, and/or the like.

The ultraviolet radiation sources 18 can operate over a wide range of wavelengths that span the ultraviolet radiation spectrum. For example, in one embodiment, the ultraviolet radiation sources 18 can operate with a wavelength that ranges from 250 nm to 360 nm. In general, for adequate optimization the wavelength range of the ultraviolet radiation sources 18 can be selected to be significantly narrower to cover 270 nm to 320 nm, and in some cases depending on the optimization target, the wavelength range can extend from 280 nm to 300 nm.

In one embodiment, the set of ultraviolet radiation sources 18 can each operate at a different peak wavelength ($\lambda$). For example, the ultraviolet radiation source $\lambda_{11}$ at the location 1,1 in the array 16 can operate at a peak wavelength of $\lambda_1$, the source $\lambda_{12}$ at the location 1,2 can operate at a peak wavelength of $\lambda_2$, the source $\lambda_{14}$ at the location 1,4 can operate at a peak wavelength of $\lambda_3$, the source $\lambda_{15}$ at the location 1,5 can operate at a peak wavelength of $\lambda_4$, and, so forth. In another embodiment, at least one of the sources in the array 16 of ultraviolet radiation sources 18 can operate at a wavelength with a peak emission at 295 nm with a full width half max ranging from 5 nm to 10 nm. It is understood, that these are only few implementations of peak wavelengths for the ultraviolet radiation sources 18 and are not meant to be limiting.

The capability of the ultraviolet radiation sources 18 to irradiate the surface 12 of the object 14 will depend on where the lighting system 10 is installed, the distance that the surface 12 of the object 14 is away from the system, an angle at which the radiation impacts the surface, etc. In one embodiment, where the ultraviolet radiation sources 18 include ultraviolet LEDs, each of the LEDs can irradiate at least a portion of the surface 12 of the object 14 from distances that range from a few centimeters to a meter. In one embodiment, the ultraviolet radiation sources 18 such as the ultraviolet LEDs can be equipped with optical elements to focus the ultraviolet radiation to a particular portion of the surface 12 of the object 14. Examples of optical elements that can be used with the ultraviolet radiation sources 18 can include, but are not limited to, mirrors, lenses, prisms, etc.

The light sensors 20 can include a variety of sensors that can detect light reflected from the surface 12 of the object 14. For example, the light sensors 20 can include, but are not limited to, photodetectors, photodiodes, and the like, that can detect light reflected from the surface 12. In one embodiment, the light sensors 20 can include light reflectance sensors that can detect radiation reflected from the surface 12 of the object 14 including fluorescent and infrared radiation. In one embodiment, the light reflectance sensors can be used to detect reflected radiation having time dependent characteristics that is generated from ultraviolet radiation sources 18 operating in a pulsed regime. In this manner, the light reflectance sensors can measure a phase-shift and a wavelength-shift of the reflected radiation from the surface 12. The light sensors 20 can also include light intensity sensors that can detect the intensity of the radiation at the surface 12 of the object 14. In another embodiment, the light sensors 20 can include fluorescent sensors to detect fluorescent radiation reflected from the surface 12 of the object 14. The light sensors 20 can include infrared sensors to detect infrared radiation reflected from the surface 12 of the object 14. In still another embodiment, the light sensors 20 can include at least one visible camera to acquire image date corresponding to the visible fluorescent radiation from the surface of the object 14.

The controller 22 can include various components to facilitate the operation of the lighting system 10 including the aspect of controlling the irradiation of the surface 12 of the object 14 with the array 16 of ultraviolet radiation sources 18, including controlling the wavelength, the intensity, the dosage and frequency of the radiation, based on feedback from the light sensors 20. For example, the controller 22 can include a timer with switches and/or the like, to manage the duration that the ultraviolet radiation sources 18 are on for a particular application. To this extent, use of the timer can ensure that radiation including spot irradiation is applied to the surface of the object 12 for that duration (e.g., a dosage timer). This includes scenarios where the ultraviolet radiation sources 18 operate in a pulsed regime. In one embodiment, each of the ultraviolet radiation sources 18 in the array 16 can deliver ultraviolet radiation to the surface 12 of the object 14 in short pulses. For example, the duration of the short pulses can include pulses of a duration and/or separated by a duration on the order of a millisecond.

The time between pulses can be selected to allow the array 16 of ultraviolet radiation sources 18 to cool a desired amount before emitting the next pulse. In one embodiment, each pulse of ultraviolet radiation generated from an ultraviolet radiation source 18 can be less than an amount of time needed for achieving a steady state temperature of operating the ultraviolet radiation source. This facilitates operation of the ultraviolet light emitting devices at a sufficiently low temperature for reliable operation. As described herein, each pulse of ultraviolet radiation generated from an ultraviolet radiation source 18 can be followed by a pause to reduce the temperature of the ultraviolet radiation source. In one embodiment, the pauses in pulses in each of the ultraviolet radiation sources 18 can reduce a temperature of the array 16 to a level that differs from an ambient temperature by at most 50%. In another embodiment, the pauses in pulses in each of the ultraviolet radiation sources 18 can reduce the temperature of the array to a level that differs from the ambient temperature by at most 20%.

In an embodiment in which the object 14 is a plant and the lighting system 10 is used to facilitate the growth of the plant, the timer can be used to coordinate the active operation of the radiation sources to correspond with the amount of daylight in a particular day, and inactivate the sources during nighttime hours. For example, the array 16 of ultraviolet radiation sources 18 can be scheduled to irradiate the surface 12 of the object 14 for a predetermined duration that is no more than six hours per day. For example, the timer can be used facilitate an illumination of the object 14 over a period of several days. In this manner, the controller 22 can detect any changes that occur on the irradiated surface (e.g., changes in size and color of the surface as well as changes in fluorescence of the surface) and store such results for future analysis. In one embodiment, the controller 20 operating in conjunction with the timer can manage the amount of time that the ultraviolet radiation sources 18 radiate in the UV-A range versus the UV-B range. The duration and frequency treatment that the ultraviolet radiation sources 18 are utilized can depend on detected condition signals provided to the controller 22 by any of the sensors 20.

The controller 22 can also be used turn off the ultraviolet radiation sources 18 upon any detected conditions provided by any of the light sensors 20. For example, the controller 22 can be configured to interrupt the operation of the ultraviolet radiation sources 18 in response to receiving light intensity signals from the light sensors 20 and determining that the light intensity at the surface 12 of the object 14 has exceeded an acceptable variation with a predetermined intensity value targeted for the surface. For example, in one embodiment, if the controller 22 determines that any of the ultraviolet radiation sources 18 is illuminating the surface of the object at a dose that delivers the ultraviolet radiation at an intensity that has exceeded an acceptable variation with the predetermined intensity value that is at most 5%, then controller 22 can instruct the power component 24 to power off the sources.

In one embodiment, the controller 22 can include a memory storage capable of recording the various data obtained from the light sensors 20. To this extent, the controller 22 can retrieve the data for further analysis and optimization of the irradiation settings.

In one embodiment, the controller 22 can also include a wireless transmitter and receiver that is configured to communicate with a remote location via Wi-Fi, BLUETOOTH, and/or the like. As used herein, a remote location is a location that is apart from the lighting system 10. For example, a remote computer can be used to transmit operational instructions to the wireless transmitter and receiver. The operational instructions can be used to program functions performed and managed by the controller 22. In another embodiment, the wireless transmitter and receiver can transmit data calculations (e.g., changes), and data from the sensors to the remote computer.

In one embodiment, the controller 22 can include an input component and an output component to allow a user to interact with the lighting system 10 and to receive information regarding the surface 12 of the object 14 and the treatment thereto with the ultraviolet radiation sources 18. In one embodiment, the input component can permit a user to select one of two modes of operating the lighting system 10. For example, the two modes of operation can include a surface disinfection mode and a plant growth promotion mode. Each of these modes can be characterized by its power spectral density and intensity of irradiation. In one embodiment, the input component can permit a user to adjust at least one of the aforementioned plurality of operating parameters. This can include making adjustments during the operation of the ultraviolet radiation sources 18 and/or prior to initiating a treatment. In one embodiment, the input component can include a set of buttons and/or a touch screen to enable a user to specify various input selections regarding the operating parameters. In one embodiment, the output component can include a visual display for providing status information on the irradiation of the object (e.g., time remaining, light intensity), status information of the object (e.g., changes in shape and size), a simple visual indicator that displays whether irradiation is underway (e.g., an illuminated light), or if the irradiation is over (e.g., absence of an illuminated light).

The controller 22 can be configured to operate within the lighting system 10 in one of a number of implementations. For example, as shown in FIG. 1, the controller 22 can be implemented as a centralized on-board control unit for the ultraviolet radiation sources 18 and the light sensors 20. In another embodiment, the controller 22 can be distributed throughout the lighting system 10. For example, the controller 22 can be distributed with the various components of the lighting system 10, such that a portion of the controller is implemented with the array of ultraviolet radiation sources 18 and light sensors 20. In another embodiment, the controller can be implemented with each individual source and sensor to perform individual control of that particular component or groups of components.

In addition to powering the ultraviolet radiation sources 18, the power component 24 is configured to provide power to the light sensors 20, the controller and any other components that can be used with the lighting system 10. In one embodiment, the power component 24 can take the form of one or more batteries, a vibration power generator that can generate power based on magnetic inducted oscillations or stresses developed on a piezoelectric crystal, and/or the like. In another embodiment, the power component 24 can include a super capacitor that is rechargeable. Other elements that are suitable for use as the power component 24 can include a mechanical energy to electrical energy converter such as a piezoelectric crystal, and a rechargeable device.

The aforementioned components of the lighting system 10 are only illustrative of one possible configuration. It is understood that the lighting system 10 can utilize other components in addition to, or in place of those described herein. These additional components can perform similar functions to those described herein, different ones, or functions that complement the operation of the ultraviolet radiation sources 18, the light sensors 20 and the controller 22. The type of additional components and functionalities that are performed will depend on the type of light sensitive object that is to be irradiated and the result that is desired through irradiation by the sources.

In one embodiment, the array 16 can include a set of visible light sources, interspersed with the ultraviolet radiation sources 18 and the light sensors 20, to irradiate the surface 12 of the object 14 with visible radiation. The set of visible light sources can irradiate the surface 12 of the object 14 in conjunction with the ultraviolet radiation sources 18. In one embodiment, the set of visible light sources can include at least one blue light source and at least one red light source. It is understood that the visible light sources can be implemented apart from the ultraviolet radiation sources 18. Examples of visible light sources can include, but are not limited to, light emitting diodes, fluorescent lighting, incandescent lighting, and/or the like. In one embodiment, the visible light sources can include a set of light emitting diodes (LEDs) operating in a blue, green, and red range. The visible set of LEDs in the array can be operated to provide a sufficient intensity of light to allow for plant growth.

In one embodiment, the array 16 can include a set of infrared sources, interspersed with the ultraviolet radiation sources 18 and the light sensors 20, as well as the visible light sources, to irradiate the surface 12 of the object 14 with infrared radiation. Examples of infrared sources can include, but are not limited to, light emitting diodes, incandescent sources, and/or the like. It is understood that the infrared sources can be implemented outside of the array 16 of the ultraviolet radiation sources 18 and the light sensors 20.

The sets of visible light sources and infrared sources can each include a variety of sources that operate over a wide range of wavelengths. Generally, the sets of visible light sources and infrared sources can irradiate an entirety of the surface 12 of the object 14 with a wavelength that ranges from 430 nm to 800 nm. In one embodiment, the set of visible light sources can include a dark blue visible light source operating in a wavelength ranging from 440 nm to 450 nm, a blue visible light source operating at a peak wavelength of 470 nm and a full width half max ranging from 5 nm to 10 nm, a green visible light source operating in a wavelength ranging from 525 nm to 540 nm, a red visible light source operating in a wavelength ranging from 620 nm to 640 nm, a red visible light source operating at a peak wavelength of 660 nm and a full width half max ranging from 5 nm to 10 nm, while the set of infrared sources can operate in a wavelength ranging from 725 nm to 740 nm. In this embodiment, the array 16 of ultraviolet radiation sources 18 can include a UV-A source operating at a peak wavelength of 365 nm with a full width half max ranging from 5 nm to 10 nm, and a UV-B source operating in a wavelength range of 280 nm to 300 nm. It is assumed that for these values, the peak wavelength is defined to within 1 nm to 5 nm.

Sets of these visible light sources and infrared sources that are configured to operate with the aforementioned wavelengths can be beneficial when considering, for example, treatments and irradiation of plants. The visible and infrared light can be beneficial for plant growth and plant photosynthesis, while the ultraviolet radiation can be beneficial for production of flavonoids within a plant. In one embodiment, the visible light sources can irradiate the surface 12 of the light sensitive object 14 with a wavelength that ranges from 430 nm to 560 nm. In another embodiment, the visible light sources can irradiate the surface 12 of the light sensitive object 14 with a wavelength that ranges from 600 nm to 800 nm.

In one embodiment, where the object 14 is a plant, the sets of visible light sources and infrared sources can be configured to irradiate the plant according to a schedule that follows the amount of daylight and darkness in a given day of a year for a given location. That is, the set of visible light sources and infrared sources can be operational to irradiate the plant during daylight hours and inoperative during nighttime hours. For example, LEDs operating in a blue, a green, and a red range can be operated to provide a sufficient intensity of light to allow for plant growth, while an infrared set of LEDs can be operated to provide control over the temperature environment of the plant.

In another embodiment where the object 14 is a plant, the ultraviolet radiation sources, the visible light sources, and the infrared sources can be implemented as a grow lamp fixture with adjustable intensities that are configured to operate in various modes. For example, the grow lamp fixture can include a dark blue source that is approximately 10% of intensity of the grow lamp fixture; a blue source that is approximately 5% of the intensity of the grow lamp fixture; a green source that is approximately 5% of the intensity of the grow lamp fixture; a red source that is approximately 20% of intensity of the grow lamp fixture; a red 660 source that is approximately 50% of the intensity of the grow lamp fixture; an infrared source that is 5% of the grow lamp fixture; a UV-A source that is approximately 5% of the intensity of the grow lamp fixture; and a UV-B source that is approximately 5% of the intensity of the grow lamp fixture. The chosen percentages can be based on the current state of the art research and experimentation for optimal growth of different type of plants. In particular, such a combination is currently understood to be advantageous for growth of Cannabaceae family of plants. It is understood that some derivation from above schedule is allowable. In particular a deviation of about 50% of the stated percent values can be utilized.

It is understood that the lighting system 10 can include other radiation sources in addition to, or in place of, the set of visible light sources and infrared sources. For example, fluorescent lights, high pressure sodium lights, metal halide lamps, and any other high intensity discharge lamps that are typically employed for growth of plants can be used with, or in place of the set of visible light sources and infrared sources. In one embodiment, the lighting system 10 can include a set of fluorescent sources to irradiate the surface 12 of the object 14 in conjunction with the ultraviolet radiation sources 18, and a set of fluorescent sensors to detect fluorescent radiation reflected from the surface 12 of the object 14.

In one embodiment, the fluorescent radiation sources and the fluorescent sensors can operate in a pulsed regime to differentiate from the fluorescent signals reflected from the surface that arise from the irradiation by the ultraviolet radiation sources 18. Alternatively, the sources of fluorescent signals can be filtered by wavelength to result in a clear collection of fluorescent signals from the surface 12 of the light sensitive object 14. It is understood that any timing for delivering the radiation to the light sensitive surface and collecting the fluorescent signal from the surface is possible. In an embodiment, a time resolved fluorescence can be employed, wherein the fluorescent radiation source can operate in a pulsed regime and the fluorescent data can be collected as the fluorescent signal is decaying. This method is known also as a transient fluorescent response as it allows for determining the lifetime of fluorescence, and possibly a phase delay between a harmonic excitation and a response which can lead to a particular sensing signature for the light sensitive surface 12.

In one embodiment, a set of test radiation sources can be utilized for performing one of a variety of analyses relating to the irradiation of the object 14. The set of test sources can include, but are not limited to, light emitting diodes, Xeon lamp source, a mercury lamp, etc. In one embodiment, the set of test sources can be used to induce fluorescent signals from the surface 12 of the object 14, while a set of fluorescent sensors can be used to detect the signals and provide them to the controller 22. In one embodiment, the test sources can include fluorescent sources such as ultraviolet radiation sources operating in a pulsed mode at peak wavelengths. The peak wavelengths of the test sources can be different from the peak wavelengths of the ultraviolet radiation sources 18 that are also used to irradiate the surface 12 of the object 14.

The controller 22 can receive the fluorescent signals from the fluorescent sensors as well any other sensors that are collecting data relating to the irradiation of the surface 12 of the object 14 by the sources. In one embodiment, the controller 22 can perform an analysis on the measurements to determine the presence of flavonoids within the plant, to attest the chemical content of the surface material base on fluorescence data, and/or the like. Generally, the analysis can include irradiating the object surface with ultraviolet light, receiving the fluorescence light data, and comparing the fluorescence light data with existing tabulated values to attest the properties of the material comprising the surface of the object. It is understood that the analysis can be performed as the controller 22 receives the fluorescent signals, or the analysis can be performed after all of the signals have been received and recorded in a storage (memory, database, etc.).

In one embodiment, other types of ultraviolet radiation sources can be used in addition to the UV-A and UV-B radiation sources. For example, UV-C radiation sources can be used to disinfect the surface 12 of the object 14 and remove bacterial or fungi contamination therefrom. In one embodiment, solid stave UV-C radiation sources operating in the wavelength range of 260 nm to 280 nm can be used for disinfection and removal of contaminants from the surface.

The lighting system 10 can further include additional sensors that can measure a plurality of conditions associated with irradiating the light sensitive object 14. In an embodiment in which the light sensitive object 12 is a plant and the application of the lighting system 10 is to facilitate growth of the plant, the additional sensors can include a set of environmental condition sensors that detect conditions of the environment in which the plant is located during irradiation by the ultraviolet radiation sources 18 and any other sources such as visible light sources and infrared sources. In one embodiment, the environmental condition sensors can include a temperature sensor, a humidity sensor, a $CO_2$ sensor, a water sensor, and a nutrient sensor. For example, a temperature sensor can measure the temperature surrounding the plant, the humidity sensor can measure the humidity surrounding the plant, the $CO_2$ sensor can measure the $CO_2$ levels surrounding the plant, a water sensor can measure an amount of water surrounding the plant or on the leaves, branches, etc., while the nutrient sensor can measure the presence of various nutrients (e.g., nitrogen (N), phosphorus (P), potassium (K), calcium (Ca), sulfur (S), magnesium (Mg), sodium (Na), etc.) in the plant. These environmental condition sensors are only illustrative of a few possibilities, and it is understood that other sensors can be used to obtain environmental conditions related to the growth of a plant or plants in a controlled environment such as greenhouses, warehouses, etc. For example, an air pressure sensor can measure the air pressure of the location in which the plant is located, and an air movement sensor can measure the air speed in close proximity to the plant.

The lighting system 10 can include other sensors in addition to the environmental condition sensors. For example, the lighting system 10 can include sensors that measure operational data associated with the irradiation by the ultraviolet radiation sources and any other sources. Other examples of sensors that can be used in the lighting system 10 can include, but are not limited to, chemical sensors, temperature sensors, humidity sensors, and/or the like. Those skilled in the art will appreciate that the type and amount of sensors used with the lighting system 10 can vary, and will depend on what the light sensitive object 14 comprises and the application or reason for irradiating the object.

In one embodiment, in which the object 14 is a plant, the controller 22 can control the irradiation by the ultraviolet radiation sources 18 and any other sources including, but not limited to, the visible light sources, the infrared sources and the fluorescent sources according to a predetermined optimal irradiation settings specified for various environmental conditions in which the plant is located. The controller 22 can adjust the irradiation settings of the sources as a function of the measurements obtained by the light sensors 20 as well as any of the other types sensors mentioned above. That is, the controller 22 can use the measurement data from the sensors as feedback to adjust the power of the sources and the settings of the sources such as, but not limited to, wavelength, dosage, intensity, frequency, in order to facilitate growth and impart change to the plant. In one embodiment, the controller 22 can use the data feedback from the sensors to detect changes in the plant that include, but are not limited to, size, shape, color, temperature and overall harvest yield. In this manner, the controller 22 can control the radiation sources to operate at a target wavelength and intensity with an intensity distribution pattern for a duration that is designed to attain a certain effect in the plant (e.g., increase production of a certain flavonoid and/or antioxidants). It is understood that, the controller 22 can use feedback of measurements from the sensors 20 to adjust any combination of various aspects of the irradiation of the plant such as wavelength, intensity, duration, and/or the like, of the irradiation.

In embodiments in which the object 12 is a living organism such as a person or an animal, the lighting system 10 can be used to apply a medical treatment, the environmental conditions can include various vital signs such as, for example, blood pressure, heart rate, temperature, pulse, humidity of the skin, and reflectivity of the skin. In this embodiment, sensors can be used to obtain vital signs such as, for example, blood pressure, heart rate, temperature, pulse, humidity of the skin, and reflectivity of the skin. In one embodiment, the controller 22 can use the data feedback from the sensors that contain vital sign data to detect changes in a person or an animal.

Figure 2:
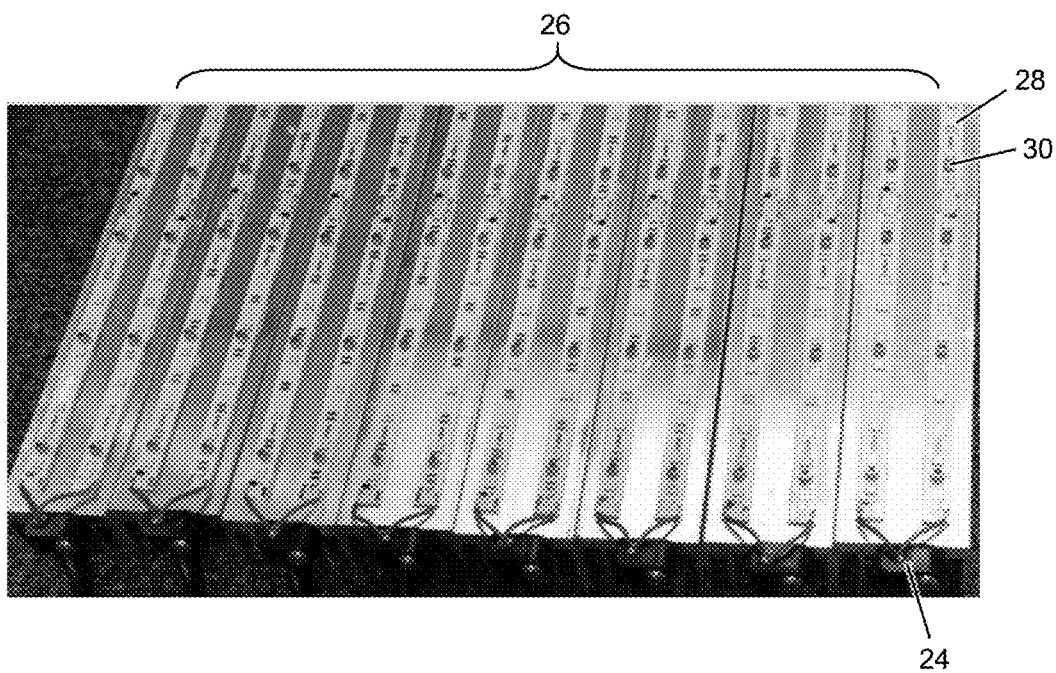
FIG. 2 shows a set of elongated structures each having radiation sources that can be deployed in a lighting system for irradiating a surface of a light sensitive object with a predetermined light intensity distribution according to an embodiment.

FIG. 2 shows a plurality 26 of elongated structures 28, each having radiation sources 30 that can be deployed in a lighting system for irradiating a surface of a light sensitive object with a predetermined light intensity distribution according to an embodiment. The radiation sources 30 in each structure 28 can include, but are not limited to, ultraviolet radiation sources, visible light sources, infrared sources, fluorescent sources and combinations thereof. The radiation sources 30 can be powered by a power component 24. In one embodiment, as shown in FIG. 2, a power component 24 can power two elongated structures 28. However, it is understood that the radiation sources 30 of the structures 28 can be powered with other configurations. For example, each structure 28 can be powered by its own corresponding power component. In another embodiment, a single power component 24 can be used to power all of the radiation sources 30 in the set 26.

Although not shown in FIG. 2, the plurality 26 of elongated structures 28 having radiation sources 30 can be implemented in a lighting system having any combination of the components described herein. For example, a controller and light sensors can be deployed with the plurality 26 of elongated structures 28 having radiation sources 30. In addition, depending on the application of the lighting system with the elongated structures, other sensors such as light sensors, fluorescent sensors and any of the environment condition sensors and sensors that measure operational data associated with the irradiation can be used with the radiation sources 30. In one embodiment, the sensors can be interspersed with the radiation sources 30 in each of the structures 28.

Figure 3:
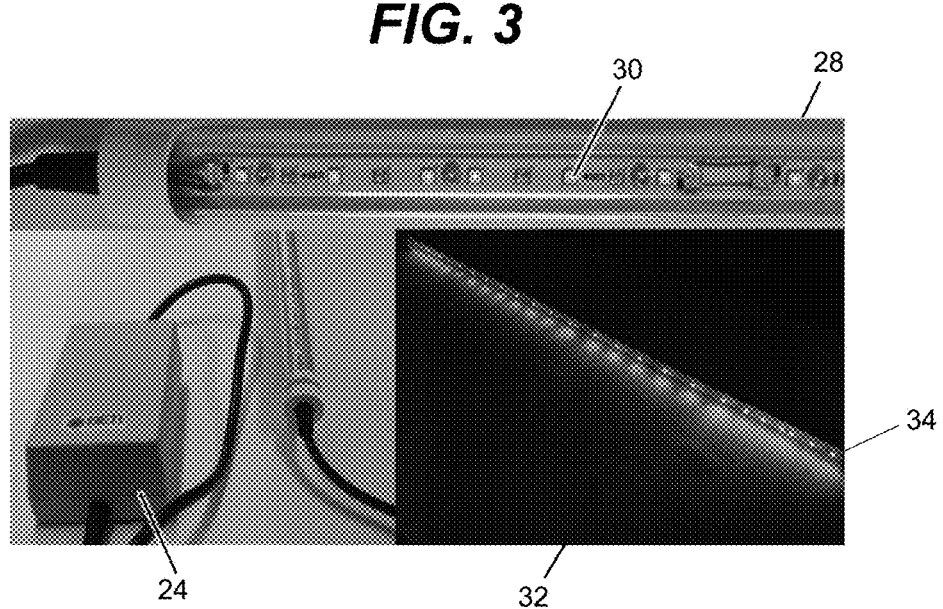
FIG. 3 shows a more detailed view of one of the elongated structures depicted in FIG. 2 with its radiation sources in operation according to an embodiment.

FIG. 3 shows a more detailed view of one of the elongated structures 28 depicted in FIG. 2 with its radiation sources 30 in operation over an area 32 according to an embodiment.

Figure 4:
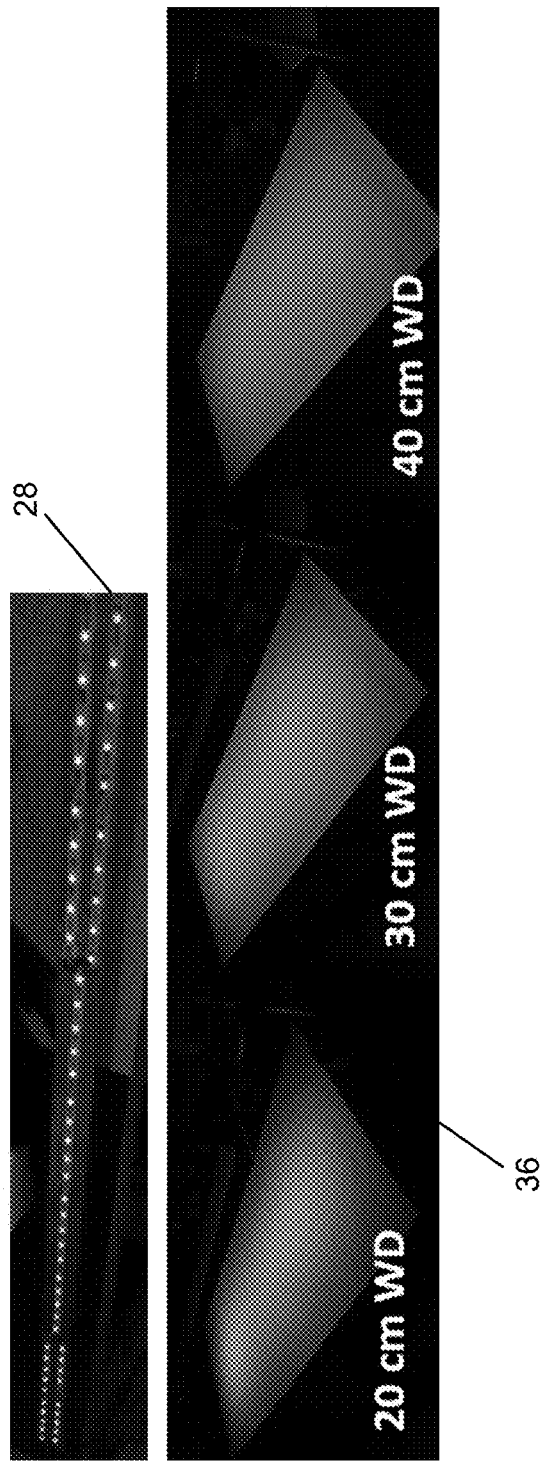
FIG. 4 shows examples of light intensity distributions that are obtained with one of the elongated structures depicted in FIG. 2 over different distances from an area irradiated by the structures according to an embodiment.

FIG. 4 shows another view of one of the elongated structures 28 depicted in FIG. 2 with its radiation sources 30 in operation along with illustrative light intensity distributions 36 obtained at various distances from an area that is irradiated with the elongated structure according to an embodiment. In one example, a light intensity distribution 36 was obtained from an implementation having a distance of 20 centimeters (cm) separating the elongated structure 28 and the area irradiated by the structure. Other light intensity distributions shown in FIG. 4 were obtained at a distance of 30 cm and 40 cm. As shown in FIG. 4, the light intensity distribution over an area irradiated by the radiation sources from the elongated structure 28 is uniform over the various distances. In particular, the light intensity distribution generated from the elongated structure 28 is not impaired as the distance between the irradiated area and the sources of the structure increases from 20 cm to 30 cm and to 40 cm.

Figure 5B:
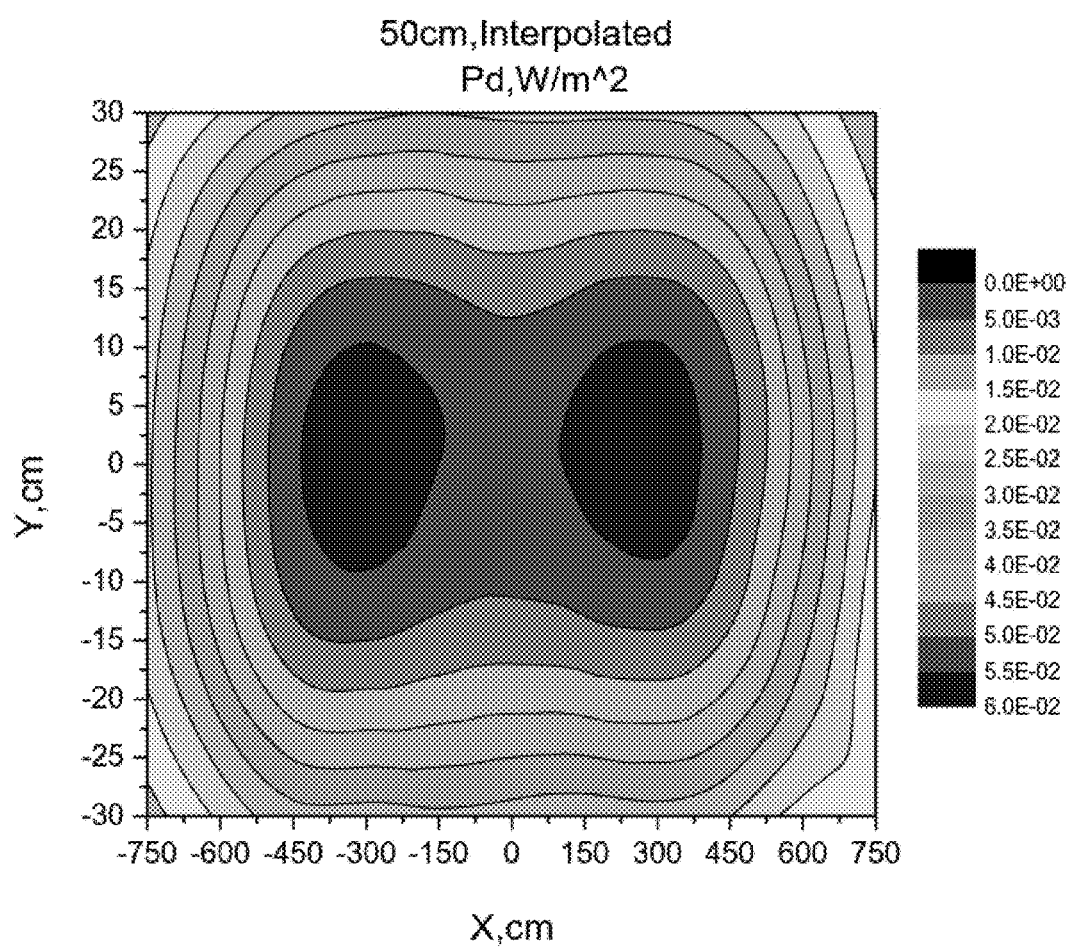

FIGS. 5A-5B show measured light intensity distributions obtained from a lighting system described herein according to an embodiment. Both of the light intensity distributions in FIGS. 5A-5B were obtained from a lighting system configured with a target objective to control the light intensity distribution over an area irradiated by the system to have a low variation. As used herein, a low variation in light intensity distribution means a uniform intensity. In the examples of FIGS. 5A-5B, the lighting system was configured to control the light intensity distribution over the area irradiated by the system to have a variation of intensity. It is understood that the lighting system could be configured to control the light intensity distribution with other variations.

The light intensity distributions of FIGS. 5A-5B were obtained at varying distances separating the lighting system and the area irradiated by the system. In particular, the light intensity distribution of FIG. 5A was obtained at an implementation where the lighting system is separated from the area undergoing irradiation by 30 cm, while the light intensity distribution of FIG. 5B was obtained at a separation distance of 50 cm. As shown in FIG. 5A, the light intensity distribution is characterized by a colored contour plot with each color corresponding to the intensity value and reported in $W/m^2$. The differences between the light intensity distributions of FIGS. 5A and 5B are due to a distance between the illumination source from the surface. In particular, in FIG. 5A the source is positioned 30 cm above the surface, while in FIG. 5B the source is positioned 50 cm above the surface.

As noted above, the lighting system of the various embodiments described herein is well suited for use with irradiating a plant. It is well known that ultraviolet radiation can affect various mechanisms of a plant. For example, plants use sunlight as an energy source and as an important environmental signal to regulate growth and development. Higher plants, such as the model plant Arabidopsis thaliana (Arabidopsis) use sunlight signals to regulate a whole range of developmental processes and adaptations including germination, de-etiolation, shade avoidance, stomatal development, circadian rhythm, and flowering. More details of the effect that ultraviolet light has on the regulation of growth and development of a plant including the signaling pathways of ultraviolet light in a plant and their transcriptional responses are described by Muller-Xing et al., "Footprints of the Sun: Memory of UV and Light Stress in Plants." *Frontiers in Plant Science*, Vol. 5 (September 2014), pp 1-11.

Because ultraviolet light can affect the various functions of plant growth and health, it is desirable that the lighting system of the various embodiments be flexible in order to adequately administer ultraviolet radiation to a plant. As mentioned above, the controller 22 is configured to control various parameters of the ultraviolet radiation that irradiates the plant based on feedback from a multitude of sensors including but not limited to, light sensors and environmental condition sensors. Examples of some the parameters that can be controlled by the controller 22 include, but are not limited to, the wavelength of ultraviolet radiation, the overall dose of ultraviolet radiation to the plant, the intensity of the ultraviolet radiation sources, the duration and frequency of the irradiation. Although different plants respond significantly different to ultraviolet radiation, the inventors of the various embodiments described herein have found that ultraviolet radiation with a peak wavelength at about 295 nm with a full width half max range of 5 nm to 20 nm is suitable for plant growth and health, while a peak wavelength at about 295 nm and a narrower full width half max range of 10 nm to 20 nm is also beneficial. In one embodiment, a dose in the range of $0.1$ $kJ/m^2$ to $20$ $kJ/m^2$ is suitable for plant growth and health.

Figure 6A:
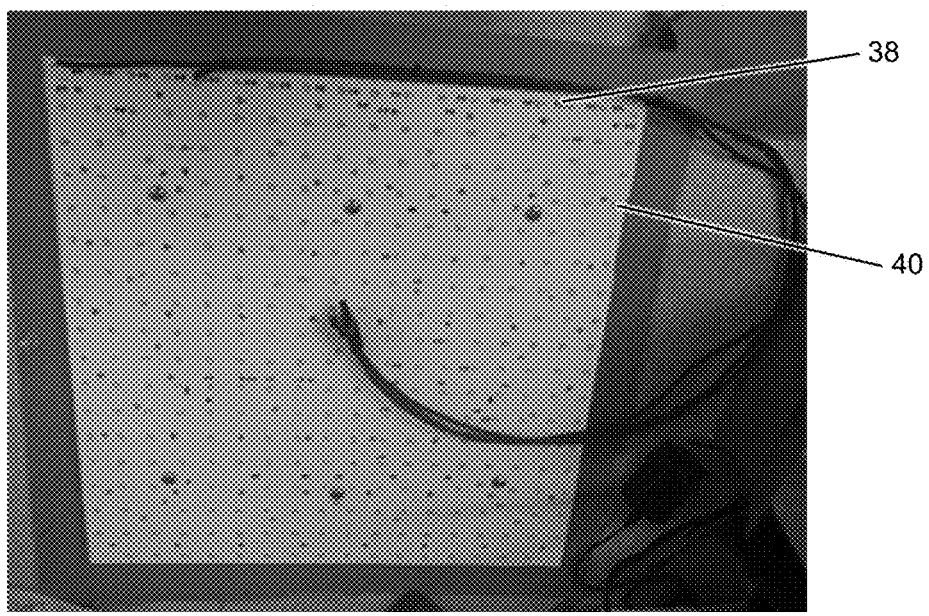
FIGS. 6A-6B show an array of radiation sources including ultraviolet radiation sources and visible light sources that can be deployed in a lighting system for irradiating a surface of a light sensitive object with a predetermined light intensity distribution according to an embodiment.
Figure 6B:
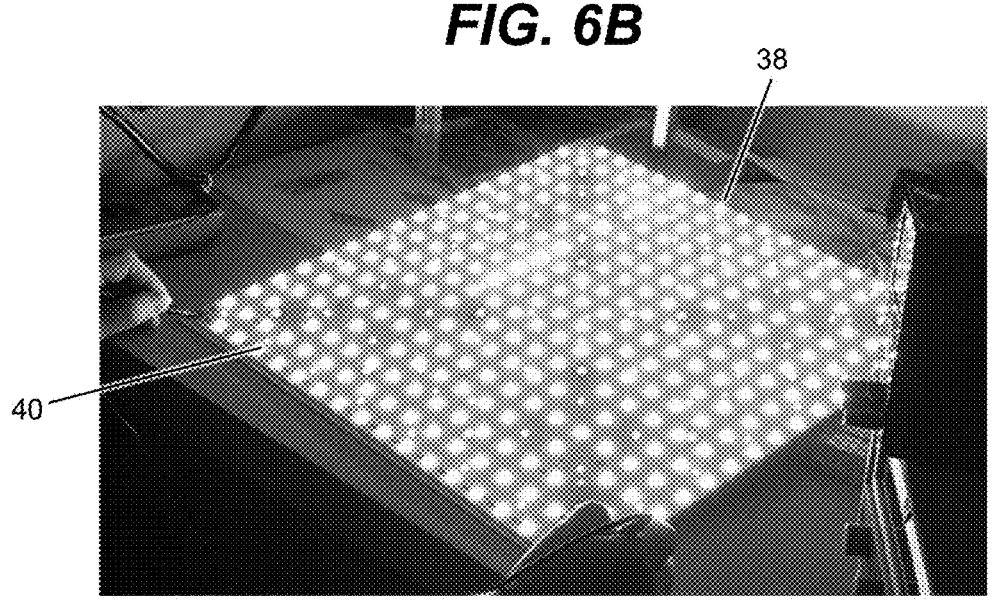

FIGS. 6A-6B show an array 38 of radiation sources 40 including ultraviolet radiation sources and visible light sources that can be deployed in a lighting system for irradiating a surface of a light sensitive object (not shown) with a predetermined light intensity distribution according to an embodiment. In particular, FIG. 6A shows the array 38 of radiation sources 40 in a non-operational state, while FIG. 6B shows the array of sources in an operational state. In one embodiment, the array 38 of radiation sources 40 can include visible light sources such as blue light sources, red light sources and white light sources and ultraviolet radiation sources. The array of visible light sources and ultraviolet radiation sources can be distributed throughout the array to provide a predetermined pattern of visible light and ultraviolet radiation to an object. It is understood that the predetermined pattern will depend on the object that is irradiated by the sources, the sources that are used in the array and the effect that is desired from the use of the sources to irradiate the object. For example, in a scenario where the object is a plant, blue light sources, red light sources and white light sources can be used to promote plant growth, while the ultraviolet radiation sources can be used to affect plant chemistry, such as affect plant flavonoid content.

Although not shown in FIGS. 6A-6B, a controller and a set of any of the aforementioned sensors can be used in conjunction with the array 38 of radiation sources 40. For example, the controller can be used to control the light intensity that is provided to the surface of the object by the radiation sources. In one embodiment, as noted above, the controller can receive light intensity measurements from the light sensors measuring the light intensity over the surface of the object, which the controller can use to determine if the light intensity from each of the sources irradiating the object is within an acceptable variation, as well as determine if the overall light intensity from all of the sources is within another predetermined variation value specified for the irradiation of the object. In one embodiment, the controller can be used to impart certain effects on the object. In the scenario where the object is a plant, the controller can use data from any of the aforementioned environment condition sensors to promote plant growth by stimulating flavonoid and an antioxidant production in the plant. For example, the controller can used the feedback measurements from the sensors to control the radiation sources to operate according to certain settings (e.g., dosage, wavelength, intensity, frequency and duration) that have been previously determined to facilitate plant growth and health under various growth conditions.

In one embodiment, the array 38 of radiation sources 40 of FIGS. 6A-6B can include an array of solid state light emitting diodes arranged in a pattern to produce an appropriate intensity distribution over a surface of an object. In addition to having a controller with the capability to monitor and maintain the light intensity provided to the surface to within a predetermined variation level, it is understood that the distance between the array 38 of radiation sources 40 and the object undergoing irradiation can be varied to a set of possible distances that have been predetermined to achieve a low variation in light intensity over the surface of the object. It is understood that the type of radiation sources including the type of light sources is variable, and the example provided above is not meant to limit the various embodiments described herein. Furthermore, it is understood that other radiation sources 40 in the array 38 can be used besides ultraviolet radiation sources and light sources. For example, the array 38 can include fluorescent radiation sources.

Figure 7:
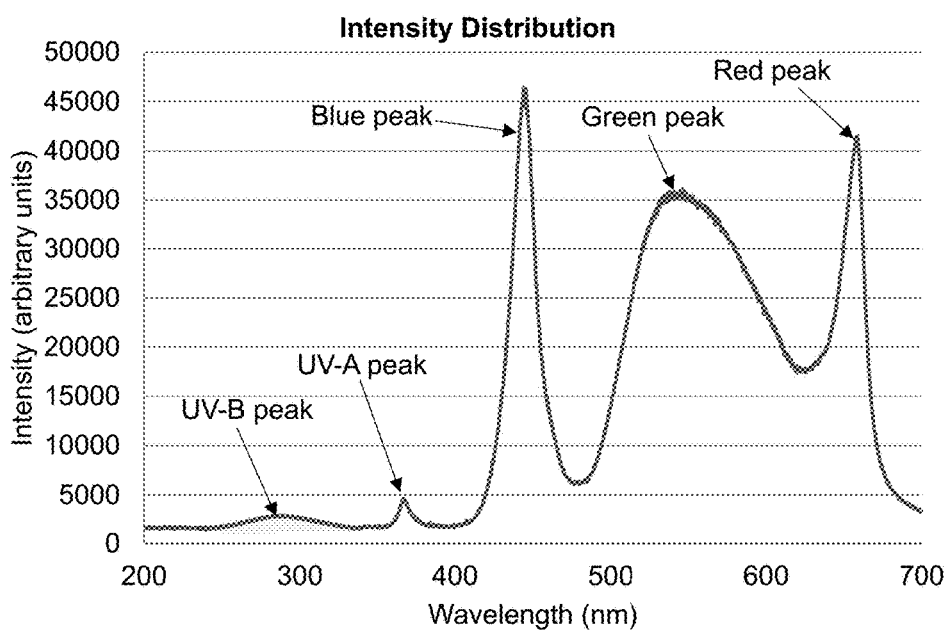
FIG. 7 shows an example of a spectral power density obtained from a lighting system described herein that has the capability to control light intensity at a surface of an object according to an embodiment.

FIG. 7 shows an example of a spectral power density that can be obtained from a lighting system described herein that has the capability to control light intensity at a surface of an object according to an embodiment. In FIG. 7, the spectral power density was obtained from a lighting system using ultraviolet radiation sources that irradiated the surface of an object with UV-A and UV-B radiation, and visible light sources that irradiated the surface with blue light, green light and red light. The presence of these sources are shown by the peaks in the spectral power density of FIG. 7. In particular, the spectral power density of FIG. 7 shows a UV-B peak wavelength of 295 nm with a full width half max ranging from 10 nm to 20 nm, a UV-A peak wavelength of about 370 nm, a blue light peak wavelength at about 450 nm, a green light peak wavelength at about 530 nm, and a red light peak wavelength at about 660 nm.

A spectral power density with this light intensity distribution provides a spectra that improves plant growth, plant health, and plant medicinal and/or antioxidant value, for a consumer. An object such as a plant that is irradiated with a lighting system that can provide such a light intensity distribution will have an effect on the plant in that the plant will have higher antioxidants and flavonoids as opposed to plant radiation with a different spectra. An important property of the disclosed spectra shows the intensity values of ultraviolet radiation in relation to visible radiation intensity values. It is understood that a lighting system using other radiation sources and/or alternative types of ultraviolet radiation sources and visible light sources operating at other parameter values can be used to attain similarly beneficial results. For example, in one embodiment, the peak wavelength of UV-B can range from 280 nm to 310 nm.

Figure 8:
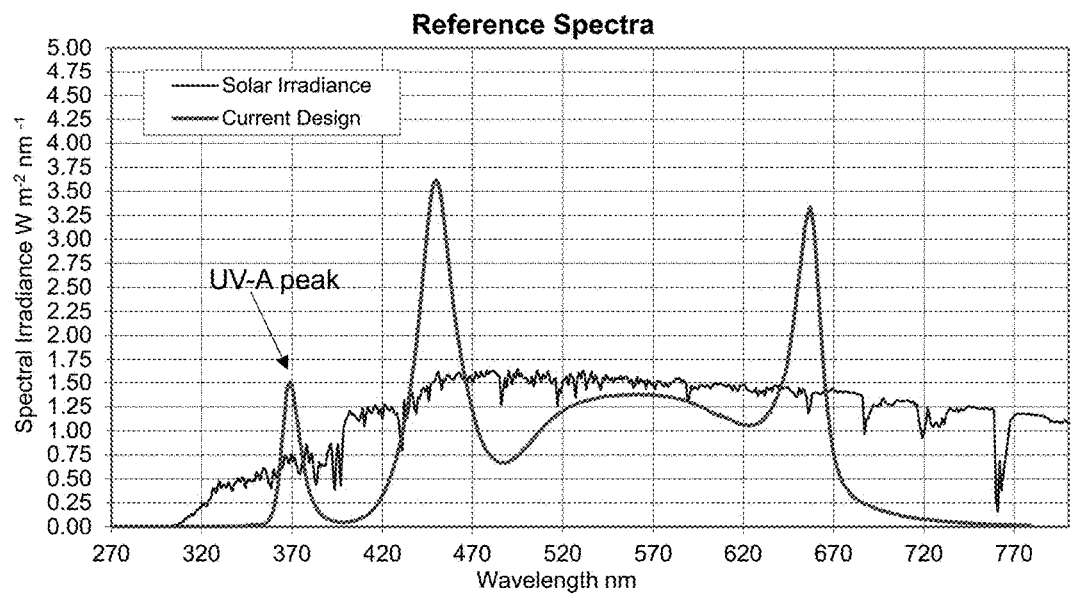
FIG. 8 shows another example of a spectral power density obtained from a lighting system described herein that has the capability to control light intensity at a surface of an object according to an embodiment.

FIG. 8 shows another example of a spectral power density obtained from a lighting system described herein that has the capability to control light intensity at a surface of an object according to an embodiment. In this example, the spectral power density of FIG. 8 was obtained from a lighting system using ultraviolet radiation sources that irradiated the surface of an object with UV-A radiation, that comprise UVA light emitting diodes, with two other peaks being correspondingly blue and red peaks. The presence of these sources are shown by the peaks in the spectral power density of FIG. 8. In particular, the spectral power density of FIG. 8 shows a UV-A peak wavelength of 370 nm, a blue peak wavelength of 450 nm, and a red peak wavelength of 650 nm.

FIG. 8 also shows the spectral power density obtained from the lighting system in relation to the spectral power density obtained from irradiating the surface of the object with solar irradiance. As shown in FIG. 8, the ultraviolet radiation spectra and blue and red spectra are amplified to improve plant health and increase plant growth. The currently selected spectra is obtained through research and experimentation to improve plant characteristics for various plant types and in particular for medicinal plants from the Cannabaceae family. Similar to FIG. 7, it is understood that for this embodiment, a lighting system using other radiation sources and/or alternative types of ultraviolet radiation sources and visible light sources operating at other parameter values can be used to attain similarly beneficial results.

Figure 9A:
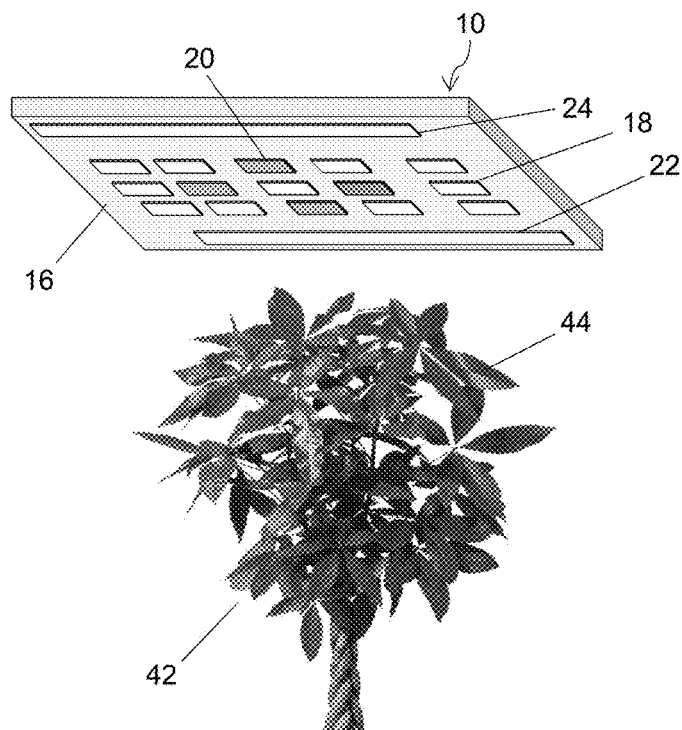
FIGS. 9A-9B show a schematic of a lighting system for irradiating a surface of a light sensitive object such as a plant at a predetermined light intensity distribution that can facilitate uniform distribution throughout the canopy of the plant according to an embodiment.
Figure 9B:
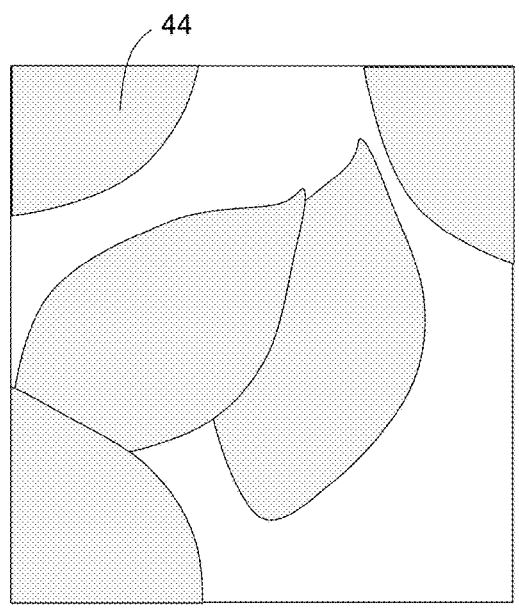

FIGS. 9A-9B show a schematic of the lighting system 10 depicted in FIG. 1 irradiating a plant 42 including its canopy of leaves 44 according to an embodiment. In the embodiments illustrated in FIGS. 9A-9B, the controller 22 of the lighting system 10 can use measurements from the light sensors 20 to ensure that the array 16 of ultraviolet radiation sources 18 irradiates the canopy of leaves 44 in the plant 42 with a uniform distribution of light intensity. Although FIG. 9A shows the lighting system 10 positioned above the plant 42, it is understood that the lighting system can be located and positioned in other orientations with respect to the plant and the canopy of leaves 44. For example, in one embodiment, the lighting system 10 can have a distributed design where the ultraviolet radiation sources and sensors do not have to be physically adjacent to each other. In an embodiment, the ultraviolet radiation source can comprise a mesh that can be located above or within the canopy of plant leaves. In this manner, the lighting system 10 with a distributed design can be located within the plant canopy.

In general, regardless of whether the lighting system 10 is positioned above the canopy of leaves 44 or in some other position such as within the canopy, irradiation of the canopy of leaves can be a complicated task for the controller 22 to facilitate a uniform distribution of light intensity. In particular, due to the three-dimensional nature of the plant canopy, not all of the leaves will receive the same dose even if the distribution of intensity over some imaginary surface that crosses the canopy is uniform.

In order to address this challenge, the controller 22 can be configured to recognize domains of the leaves 44 as two-dimensional projections. As used herein, recognizing domains of the leaves 44 as two-dimensional projections means locating the domains comprising the surfaces of leaves in three dimensional space. In this manner, the controller 22 can control the ultraviolet radiation sources 18 based on the light sensor 20 feedback to deliver the radiation at a direction and intensity that is uniform to all of the leaves in each domain. Since the projections of two-dimensional domains of leaves maps to the three-dimensional nature of the plant canopy, all of the leaves 44 in the canopy will receive a uniform distribution of light intensity.

In order to ensure that all of the two-dimensional domains of leaves receive an optimal light distribution such as a uniform light intensity distribution, the controller 22 can implement an algorithm that determines the distribution of an optimal intensity over a surface. In one embodiment, the algorithm can begin by first determining the position of the leaves in each of the domains using reflected light measurements received from the light sensors 20. In particular, the positions of leaves are determined by partitioning the space into subdomains (such as finite elements) and determining if each subdomain belongs to a surface of a leaf or not. After determining the positions of the leaves in each two-dimensional domain, the controller 22 can then record the coordinates that cover the two-dimensional image of the leaves in the domain.

Next, the controller 22 can direct the ultraviolet radiation sources to irradiate the surface area of the leaves 44 on the plant 42 that corresponds to each two-dimensional domain with light intensity having a peak distribution. In one embodiment, the light intensity with peak distribution can be directed to the center of the leaves using a set wavelength for the illumination. The light sensors 20 can measure the light intensity distribution over each of the leaves 44 that corresponds to a two-dimensional domain. The controller 22 can also record the light intensity measurements over the leaves in each two-dimensional domain.

The controller 22 can then compare the light intensity distribution over the leaves in each two-dimensional domain to a desired target intensity distribution stored in memory. In one embodiment, the desired target intensity distribution can include, but is not limited to, the coloration of the leaf, the type of leaf (size and location on the stem of the plant), etc. If the desired target intensity distribution over the leaves domain is achieved, then the intensity distribution over the surface of the leaves is deemed to be found, recorded in memory, and the process of determining the optimal intensity distribution over a surface encompassing the leaves for a particular domain is terminated. Alternatively, if the desired target intensity distribution is not attained, then the controller can instruct the power component 24 to change the power of the ultraviolet radiation sources irradiating that domain to adjust the intensity over the leaves in the domain. The comparison of light intensity measurements and adjusting of the light intensity can continue until the controller determines that the domain has achieved the desired target intensity distribution. The process would be similar for all of the other two-dimensional leave domains that form the canopy of leaves 44.

With all of the settings determined for effectuating optimal irradiation of the canopy of leaves 44, the lighting system 10 can use these settings to globally irradiate other plants in a controlled environment such as, for example, a greenhouse. These settings can also be specified for types of plants during different periods of plant growth. For example, the different periods of plant growth can include, but are not limited to, a plant seedling period, a plant development period, a plant maturity period, plant blooming period and a plant fruition period. It is understood that the optimal irradiation settings can also be specified for different parts of the plant and not just the canopy of leaves 44. For example, specific parts of the leaves 44 or sections of the plant 42 such as the trunk or roots can have vastly different irradiation conditions, and can thus have different settings which can be ascertained in a like manner.

It is understood that for a three-dimensional structure, the complexity of illumination can be due to reflection and scattering from other surfaces presented in a surrounding environment. Thus, both the power and the direction of the radiation that is emitted from the array 16 of ultraviolet radiation sources 18 can be adjusted until the optimal configuration of intensity is found. For example, the ultraviolet radiation sources 18 can be configured to have a directional degree of freedom (within a range) in order to radiate a surface at a direction characterized by two surface angles. In addition, in one embodiment, the lighting system 10 can be implemented with ultraviolet radiation sources 18 having the capability for lateral motion along a mounting surface of the system. In one embodiment, the ultraviolet radiation sources 18 can be configured as a lamp fixture in order to provide further control of intensity that can be directed to the canopy of leaves 44. It is understood, that the ultraviolet radiation sources 18 can be positioned at a density that is variable through the mounting surface. For instance, more of the ultraviolet radiation sources 18 can be positioned on the periphery of the mounting surface of the lamp fixture in order to provide a focused light intensity distribution to the area of the canopy that would be irradiated by such sources. Further, although the embodiment depicted in FIGS. 9A-9B is discussed only with regard to the ultraviolet radiation sources 18 and the light sensors 20, it is understood that the lighting system 10 can be implemented with any of the other aforementioned radiation sources (e.g., visible light sources, infrared radiation sources, fluorescent sources) and sensors (e.g., environment condition sensors, fluorescent sensors).

Figure 10:
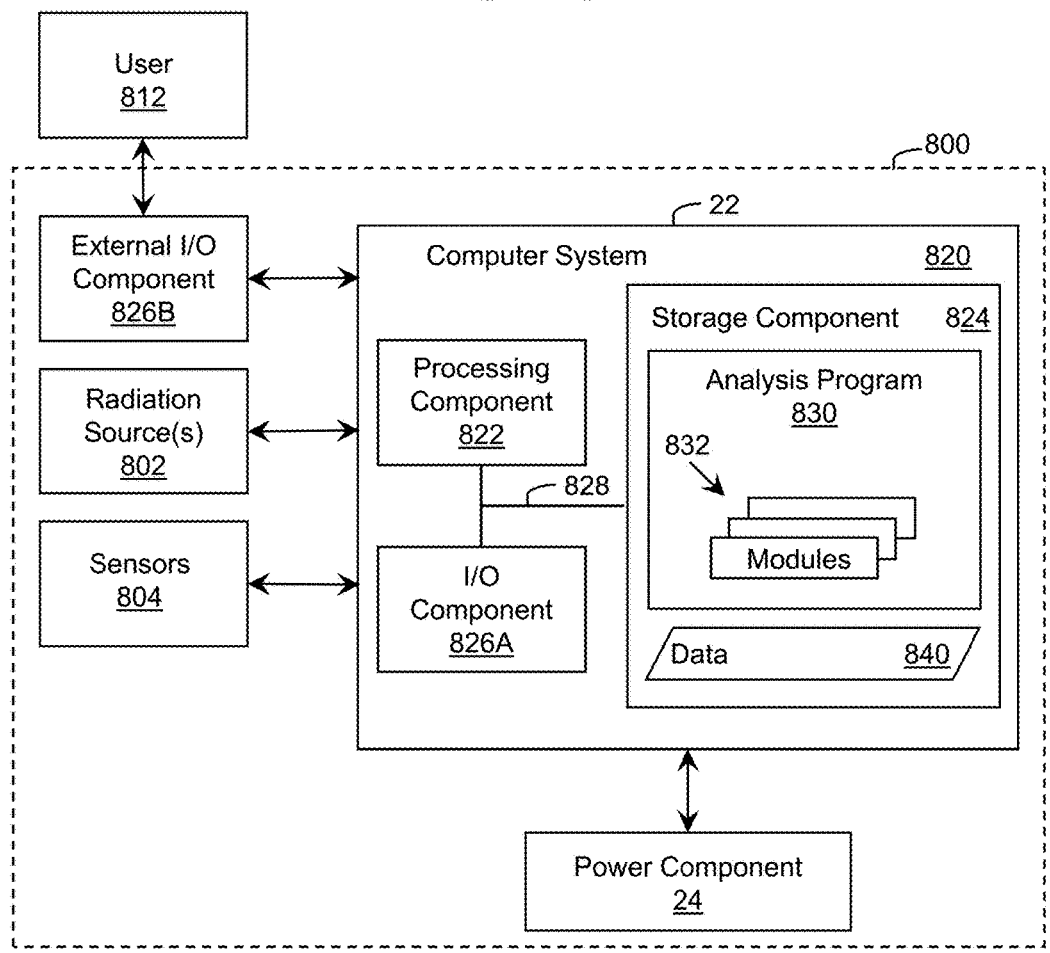
FIG. 10 shows a schematic block diagram representative of an overall processing architecture of a lighting system for irradiating a light sensitive object according to an embodiment.

Referring now to FIG. 10, there is a schematic block diagram representative of an overall processing architecture of a lighting system 800 for irradiating a light sensitive object. In this embodiment, the architecture of the lighting system 800 is shown including the radiation sources 802 (e.g. ultraviolet radiation sources, visible light sources, infrared sources, fluorescent sources) and the sensors 804 (e.g., light sensors, environment condition sensors, fluorescent sensors) for the purposes of illustrating the interaction of all of the components that can be used to provide a lighting system for irradiating a light sensitive object.

As depicted in FIG. 10 and described herein, the system 800 can include a controller 22. In one embodiment, the controller 22 can be implemented in the form of a control unit embodying a computer system 820 including an analysis program 830, which makes the computer system 820 operable to manage the radiation sources 802 and the sensors 804 in the manner described herein. In particular, the analysis program 830 can enable the computer system 820 to operate the radiation sources 802 to direct radiation towards the object and process data obtained during operation which is stored as data 840. The computer system 820 can individually control each source 802 and sensor 804 and/or control two or more of the sources and the sensors as a group. Furthermore, the radiation sources can emit radiation of substantially the same wavelength or of multiple distinct wavelengths.

In an embodiment, during an initial period of operation, the computer system 820 can acquire data from at least one of the sensors 804 regarding one or more attributes used by the lighting system and generate data 840 for further processing. The computer system 820 can use the data 840 to control one or more aspects of the radiation generated by the radiation sources 802 during testing and operational modes.

Furthermore, one or more aspects of the operation of the radiation sources 802 can be controlled or adjusted by a user 812 via an external interface I/O component 826B. The external interface I/O component 826B can be used to allow the user 812 to selectively turn on/off the radiation sources 802.

The external interface I/O component 826B can include, for example, a touch screen that can selectively display user interface controls, such as control dials, which can enable the user 812 to adjust one or more of: an intensity, and/or other operational properties of the set of radiation sources 802 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of radiation sources 802 and sensors 804. The external interface I/O component 826B also can include any combination of various output devices (e.g., an LED, a visual display), which can be operated by the computer system 820 to provide status information for use by the user 812. For example, the external interface I/O component 826B can include one or more LEDs for emitting a visual light for the user 812, e.g., to indicate a status of the irradiation of the samples. In an embodiment, the external interface I/O component 826B can include a speaker for providing an alarm (e.g., an auditory signal), e.g., for signaling that ultraviolet radiation is being generated or that an irradiation has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the sources and the sensors. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 10 can receive power from a power component 24. The power component 24 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A lighting system, comprising:
an array of ultraviolet radiation sources configured to irradiate a surface of a light sensitive surface object with ultraviolet radiation having a wavelength range that includes ultraviolet-A (UV-A) radiation and ultraviolet-B (UV-B) radiation, wherein each of the ultraviolet radiation sources operates in a predetermined wavelength range that includes at least one of: a UV-A radiation wavelength range or a UV-B radiation wavelength range, wherein at least one of the ultraviolet radiation sources operates at a peak wavelength that is within the UV-B wavelength range;
a plurality of fluorescent sources to irradiate the surface of the object in conjunction with the ultraviolet radiation sources;
a plurality of light sensors configured to measure light intensity at the surface of the object, wherein each light sensor measures light intensity in a wavelength range that corresponds to the predetermined wavelength range emitted from at least one of the ultraviolet radiation sources in the array;
a plurality of fluorescent sensors to detect fluorescent radiation reflected from the surface of the object, wherein the fluorescent sources and the fluorescent sensors operate in a pulsed regime to differentiate from fluorescent signals reflected from the surface that arise from the irradiation by the ultraviolet radiation sources; and
a controller configured to control the light intensity over the surface of the object by adjusting operational power of the ultraviolet radiation sources as a function of measurements obtained by the light sensors and the fluorescent sensors, wherein the controller uses the light intensity measurements from the light sensors to determine whether each ultraviolet radiation source is illuminating the surface of the object with an intensity that has a variation that is more than 50% of a predetermined intensity value targeted for the surface, the controller adjusting the power of an ultraviolet radiation source in response to determining that the ultraviolet radiation source is illuminating the surface of the object with an intensity that has a variation that is more than 50% of the predetermined intensity value targeted for the surface, the controller adjusting the power of the ultraviolet radiation source as a function of the variation between the light intensity generated from the source and the predetermined intensity value targeted for the surface.

2. The lighting system of claim 1, further comprising light reflectance sensors to detect radiation reflected from the surface of the object including fluorescent and infrared radiation.

3. The lighting system of claim 2, wherein the light reflectance sensors detect the reflected radiation having time dependent characteristics that is generated from ultraviolet radiation sources operating in a pulsed regime, the light reflectance sensors measuring a phase-shift and a wavelength-shift of the reflected radiation from the surface.

4. The lighting system of claim 1, wherein the controller controls the light intensity over the surface of the object to maintain a predetermined intensity distribution that is provided by the ultraviolet radiation sources, wherein the predetermined intensity distribution includes a set of points along the surface that have a minimal difference in intensity.

5. The lighting system of claim 1, wherein the light sensors are interspersed within the array of ultraviolet radiation sources.

6. A lighting system, comprising:
an array of ultraviolet radiation sources configured to irradiate a surface of a light sensitive object with ultraviolet radiation having a wavelength range that includes ultraviolet-A (UV-A) radiation and ultraviolet-B (UV-B) radiation, wherein each of the ultraviolet radiation sources irradiates the surface of the object with ultraviolet radiation over a predetermined wavelength range, and at least one of the ultraviolet radiation sources operates at a peak wavelength that is within a UV-B wavelength range;
a plurality of fluorescent sources to irradiate the surface of the object in conjunction with the ultraviolet radiation sources;
a plurality of light sensors configured to measure light intensity at the surface of the object, wherein each light sensor measures light intensity in a wavelength range that corresponds to the predetermined wavelength range emitted from at least one of the ultraviolet radiation sources in the array;
a plurality of fluorescent sensors to detect fluorescent radiation reflected from the surface of the object, wherein the fluorescent sources and the fluorescent sensors operate in a pulsed regime to differentiate from fluorescent signals reflected from the surface that arise from the irradiation by the ultraviolet radiation sources; and
a controller configured to control the light intensity over the surface of the object as a function of measurements obtained from the light sensors and the fluorescent sensors, wherein the controller uses the light intensity measurements from the light sensors to determine whether each ultraviolet radiation source is illuminating the surface of the object at a dose that delivers the ultraviolet radiation at an intensity that is within a predetermined acceptable variation of a predetermined intensity value targeted for the surface, the controller adjusting the power of an ultraviolet radiation source in response to determining that the ultraviolet radiation source is illuminating the surface with an intensity that has an unacceptable variation with the predetermined intensity value targeted for the surface, each ultraviolet radiation source that is adjusted in power delivers an adjusted dose of the ultraviolet radiation that is a function of an amount of the unacceptable variation with the predetermined intensity value.

7. The lighting system of claim 6, wherein the predetermined acceptable variation with the predetermined intensity value is at most 5%.

8. The lighting system of claim 6, wherein the dose is in the range of 0.1 kJ/m$^2$ to 20 kJ/m$^2$.

9. The lighting system of claim 6, wherein each of the ultraviolet radiation sources in the array delivers ultraviolet radiation to the surface of the object in short pulses.

10. The lighting system of claim 9, wherein each pulse of ultraviolet radiation generated from an ultraviolet radiation source is less than an amount of time needed for achieving a steady state temperature of operating the ultraviolet radiation source.

11. The lighting system of claim 6, wherein the array of ultraviolet radiation sources operate with a wavelength that ranges from 280 nm to 300 nm, and at least one of the ultraviolet radiation sources emits ultraviolet radiation with a peak emission wavelength at 295 nm with a full width half max ranging from 5 nm to 10 nm.

12. The lighting system of claim 6, wherein the array of ultraviolet radiation sources is configured for movement about the object, wherein the movement includes both translational and directional degrees of freedom.

13. The lighting system of claim 6, wherein the array of ultraviolet radiation sources includes a greater amount of ultraviolet radiation sources located at side portions of the array in comparison to an amount of ultraviolet radiation sources located near a central region of the array, wherein the side portions include at least 10% more ultraviolet radiation sources than the amount of ultraviolet radiation sources located near the central region.

14. The lighting system of claim 13, wherein the ultraviolet radiation sources located at the side portions of the array operate at a higher pulsed frequency than the ultraviolet radiation sources located near the central region.

15. The lighting system of claim 13, wherein the ultraviolet radiation sources located at the side portions of the array operate at a higher power than the ultraviolet radiation sources located near the central region.

16. The lighting system of claim 6, wherein the array of ultraviolet radiation sources includes a grow lamp fixture including a UV-A source operating at an intensity that is approximately 5% of the grow lamp fixture; and a UV-B source operating at an intensity that is approximately 5% of the grow lamp fixture.

17. The lighting system of claim 16, wherein the grow lamp fixture includes a set of visible light sources having a dark blue light source operating at an intensity that is approximately 10% of the grow lamp fixture; a blue light source operating at an intensity that is approximately 5% of the grow lamp fixture; a green light source operating at an intensity that is approximately 5% of the grow lamp fixture; a red light source operating at an intensity that is approximately 20% of the grow lamp fixture; and a red 660 light source operating at an intensity that is approximately 50% of the grow lamp fixture.

18. The lighting system of claim 16, wherein the grow lamp fixture includes an infrared source operating at an intensity that is approximately 5% of the grow lamp fixture.

19. The lighting system of claim 6, wherein at least one of the light sensors comprises a visible camera.

20. A lighting system, comprising:
an array of ultraviolet radiation sources configured to irradiate a surface of a light sensitive surface object with ultraviolet radiation having a wavelength range that includes ultraviolet-A (UV-A) radiation and ultraviolet-B (UV-B) radiation, wherein each of the ultraviolet radiation sources operates in a predetermined wavelength range that includes at least one of: a UV-A radiation wavelength range or a UV-B radiation wavelength range, wherein at least one of the ultraviolet radiation sources operates at a peak wavelength that is within the UV-B wavelength range;

a plurality of fluorescent sources to irradiate the surface of the object in conjunction with the ultraviolet radiation sources;

a plurality of light sensors configured to measure light intensity at the surface of the object, wherein each light sensor measures light intensity in a wavelength range that corresponds to the predetermined wavelength range emitted from at least one of the ultraviolet radiation sources in the array;

a plurality of fluorescent sensors to detect fluorescent radiation reflected from the surface of the object, wherein the fluorescent sources and the fluorescent sensors operate in a pulsed regime to differentiate from fluorescent signals reflected from the surface that arise from the irradiation by the ultraviolet radiation sources; and a controller configured to control the light intensity over the surface of the object by adjusting operational power of the ultraviolet radiation sources as a function of measurements obtained by the light sensors and the fluorescent sensors.

* * * * *